(12) United States Patent
Terentiev et al.

(10) Patent No.: US 7,762,716 B2
(45) Date of Patent: Jul. 27, 2010

(54) MIXING VESSEL WITH A FLUID-AGITATING ELEMENT SUPPORTED BY A ROLLER BEARING

(75) Inventors: Alexandre N. Terentiev, Lexington, KY (US); Sergey Terentyev, Lexington, KY (US)

(73) Assignee: Levtech, Inc., Lexington, KY (US)

( * ) Notice: Subject to any disclaimer, the term of this patent is extended or adjusted under 35 U.S.C. 154(b) by 1095 days.

(21) Appl. No.: 11/298,406

(22) Filed: Dec. 9, 2005

(65) Prior Publication Data

US 2006/0092761 A1    May 4, 2006

Related U.S. Application Data

(63) Continuation-in-part of application No. 10/491,512, filed on Apr. 1, 2004, now Pat. No. 7,481,572, and a continuation-in-part of application No. 10/398,946, filed as application No. PCT/US01/31459 on Oct. 9, 2001.

(60) Provisional application No. 60/634,664, filed on Dec. 9, 2004, provisional application No. 60/239,187, filed on Oct. 9, 2000, provisional application No. 60/318,579, filed on Sep. 11, 2001.

(51) Int. Cl.
B01F 7/16 (2006.01)

(52) U.S. Cl. .................. 366/273; 366/279; 366/314; 366/331; 383/127

(58) Field of Classification Search ................ 366/273, 366/274, 279, 314, 331, 241; 383/127
See application file for complete search history.

(56) References Cited

U.S. PATENT DOCUMENTS

| | | | |
|---|---|---|---|
| 2,506,886 A | 5/1950 | Okulitch et al. |
| 3,399,040 A | 8/1968 | Ilg |
| 3,647,397 A | 3/1972 | Coleman |
| 3,888,466 A | 6/1975 | Sedam |
| 3,981,803 A | 9/1976 | Coulthard |
| 4,027,427 A | 6/1977 | Stoller et al. |
| 4,040,605 A | 8/1977 | Towsend |
| 4,162,855 A | 7/1979 | Bender |
| 4,199,265 A | 4/1980 | Sanderson et al. |
| 4,209,259 A | 6/1980 | Rains et al. |
| 4,290,300 A | 9/1981 | Carver |
| 4,355,906 A | 10/1982 | Ono |

(Continued)

FOREIGN PATENT DOCUMENTS

DE    4201693    1/1992

(Continued)

OTHER PUBLICATIONS

Angelo De Palma, "Throwing it All Away The Economics of Cleaning Drive Bioprocessors to Disposable, Single-Use Components and Systems," Pharmaceutical Manufacturing, Apr./May 2004, pp. 35-40.

(Continued)

*Primary Examiner*—Tony G Soohoo
(74) *Attorney, Agent, or Firm*—King & Schickli, PLLC

(57) ABSTRACT

In a vessel, such as a flexible bag, a fluid is received and agitated using an internal fluid-agitating element driven by an external motive device and supported by a bearing, such as a roller bearing.

34 Claims, 21 Drawing Sheets

U.S. PATENT DOCUMENTS

| | | | |
|---|---|---|---|
| 4,483,623 A | 11/1984 | Eaton et al. | |
| 4,498,785 A | 2/1985 | de Bruyne | |
| 4,557,377 A | 12/1985 | Maloney | |
| 4,568,195 A | 2/1986 | Herz et al. | |
| 4,591,357 A | 5/1986 | Sneider | |
| 4,711,582 A | 12/1987 | Kennedy | |
| 4,830,511 A | 5/1989 | Smazik | |
| 4,901,886 A | 2/1990 | Kirschner | |
| 4,913,555 A | 4/1990 | Maeda et al. | |
| 4,993,840 A | 2/1991 | Maeda et al. | |
| 4,993,841 A | 2/1991 | Lofgren et al. | |
| 5,040,898 A | 8/1991 | Sweatman et al. | |
| 5,045,074 A | 9/1991 | Satterfield et al. | |
| 5,061,079 A | 10/1991 | Shiobara | |
| 5,141,327 A | 8/1992 | Shiobara | |
| 5,183,336 A | 2/1993 | Poltorak et al. | |
| 5,193,977 A | 3/1993 | Dame | |
| 5,222,808 A | 6/1993 | Sugarman et al. | |
| 5,225,346 A | 7/1993 | Matsumiya et al. | |
| 5,236,135 A * | 8/1993 | Wilson et al. | 241/21 |
| 5,240,187 A * | 8/1993 | Wilson | 241/21 |
| 5,240,322 A | 8/1993 | Haber et al. | |
| 5,240,856 A | 8/1993 | Goffe et al. | |
| 5,261,742 A | 11/1993 | Lockhart | |
| 5,267,791 A | 12/1993 | Christian et al. | |
| 5,288,296 A | 2/1994 | McCabe et al. | |
| 5,306,269 A | 4/1994 | Lewis et al. | |
| 5,350,080 A | 9/1994 | Brown et al. | |
| 5,368,390 A | 11/1994 | Gambrill et al. | |
| 5,385,546 A | 1/1995 | Kriesel et al. | |
| 5,385,564 A | 1/1995 | Slater et al. | |
| 5,393,142 A | 2/1995 | Meier | |
| 5,407,272 A | 4/1995 | Meier | |
| 5,434,079 A | 7/1995 | Mozayeni | |
| 5,445,629 A | 8/1995 | Debrauwere et al. | |
| 5,470,151 A | 11/1995 | Walthall et al. | |
| 5,478,149 A | 12/1995 | Quigg | |
| 5,533,804 A | 7/1996 | Larsson et al. | |
| 5,565,015 A | 10/1996 | Kobayashi | |
| 5,567,672 A | 10/1996 | Terentiev et al. | |
| 5,578,012 A | 11/1996 | Kamen et al. | |
| 5,586,823 A | 12/1996 | Carr | |
| 5,655,834 A * | 8/1997 | Dickson | 366/205 |
| 5,672,481 A | 9/1997 | Minshall et al. | |
| 5,676,462 A | 10/1997 | Fraczek et al. | |
| 5,733,776 A | 3/1998 | Barngrover et al. | |
| 5,758,965 A | 6/1998 | Gambrill et al. | |
| 5,779,359 A | 7/1998 | Gambrill et al. | |
| 5,794,802 A | 8/1998 | Caola | |
| 5,803,137 A | 9/1998 | Shimotoyodome et al. | |
| 5,899,567 A | 5/1999 | Morris, Jr. | |
| 5,941,635 A | 8/1999 | Stewart | |
| 5,941,867 A | 8/1999 | Kao | |
| 5,961,213 A | 10/1999 | Tsuyuki et al. | |
| 5,985,535 A | 11/1999 | Urabe | |
| 5,988,422 A | 11/1999 | Vallot | |
| 5,998,019 A | 12/1999 | Rosenbaum et al. | |
| 6,065,865 A | 5/2000 | Eyraud et al. | |
| 6,076,457 A | 6/2000 | Vallot | |
| 6,083,587 A | 7/2000 | Smith et al. | |
| 6,086,574 A | 7/2000 | Carroll et al. | |
| 6,168,862 B1 | 1/2001 | Rosenbaum et al. | |
| 6,183,460 B1 | 2/2001 | Smith et al. | |
| 6,186,932 B1 | 2/2001 | Vallot | |
| 6,206,562 B1 | 3/2001 | Eyraud et al. | |
| 6,219,871 B1 | 4/2001 | Frederick et al. | |
| 6,245,555 B1 | 6/2001 | Curtis | |
| 6,332,706 B1 | 12/2001 | Hall | |
| 6,416,215 B1 | 7/2002 | Terentiev | |
| 6,432,698 B1 | 8/2002 | Gaugler et al. | |
| 6,494,613 B2 | 12/2002 | Terentiev | |
| 6,670,171 B2 | 12/2003 | Carll | |
| 6,709,862 B2 | 3/2004 | Curtis | |
| 6,837,610 B2 | 1/2005 | Cadogan et al. | |
| 6,837,613 B2 | 1/2005 | Terentiev | |
| 7,086,778 B2 | 8/2006 | Terentiev | |
| 7,153,021 B2 | 12/2006 | Goodwin et al. | |
| 7,278,780 B2 | 10/2007 | Goodwin et al. | |
| 7,357,567 B2 | 4/2008 | Terentiev | |
| 7,384,027 B2 | 6/2008 | Terentiev et al. | |
| 7,434,983 B2 | 10/2008 | Terentiev | |
| 7,469,884 B2 | 12/2008 | Terentiev et al. | |
| 7,481,572 B2 | 1/2009 | Terentiev | |
| 2002/0105856 A1 | 8/2002 | Terentiev | |
| 2002/0131654 A1 | 9/2002 | Smith et al. | |
| 2002/0145940 A1 | 10/2002 | Terentiev | |
| 2003/0077466 A1 | 4/2003 | Smith et al. | |
| 2003/0198406 A1 | 10/2003 | Bibbo et al. | |
| 2003/0226857 A1 | 12/2003 | Bibbo et al. | |
| 2003/0231546 A1 | 12/2003 | Bibbo et al. | |
| 2004/0027912 A1 | 2/2004 | Bibbo et al. | |
| 2004/0047232 A1 | 3/2004 | Terentiev | |
| 2004/0062140 A1 | 4/2004 | Cadogan et al. | |
| 2004/0190372 A1 | 9/2004 | Goodwin et al. | |

FOREIGN PATENT DOCUMENTS

| | | |
|---|---|---|
| DE | 4413463 | 4/1994 |
| DE | 19643844 | 10/1996 |
| FR | 2696949 | 4/1994 |
| GB | 1380316 | 1/1975 |
| GB | 2202549 | 9/1988 |
| GB | 0343885 | 11/1989 |
| JP | 3127618 | 5/1991 |
| JP | 6285353 | 10/1994 |
| JP | 2000176269 | 6/2000 |

OTHER PUBLICATIONS

Steven Current "Business Plan," LevTech, Inc., Sep. 5, 2000, pp. 1, 8, 9, 11, 12, 13, and 25.

Russ Musch, "Product Brief Form for HyClone Bioprocess Containers," May 3, 2001.

"The Flexboy Mixer," www.stedim.com, 4 pages.

U.S. Appl. No. 12/250,180, filed Oct. 13, 2008, Terentiev.

* cited by examiner

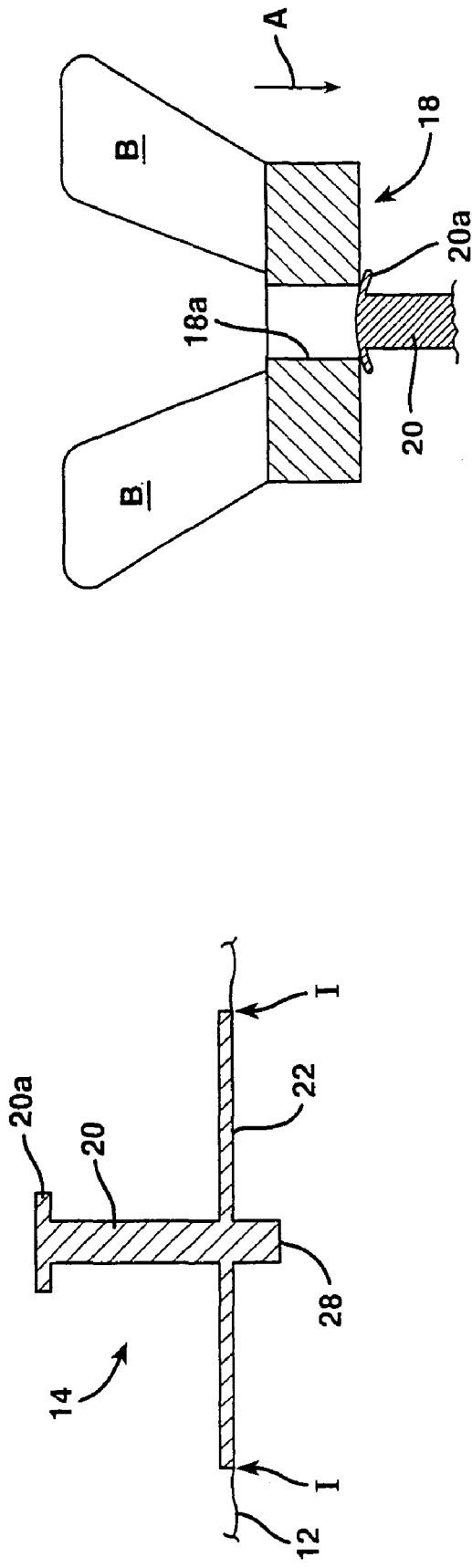

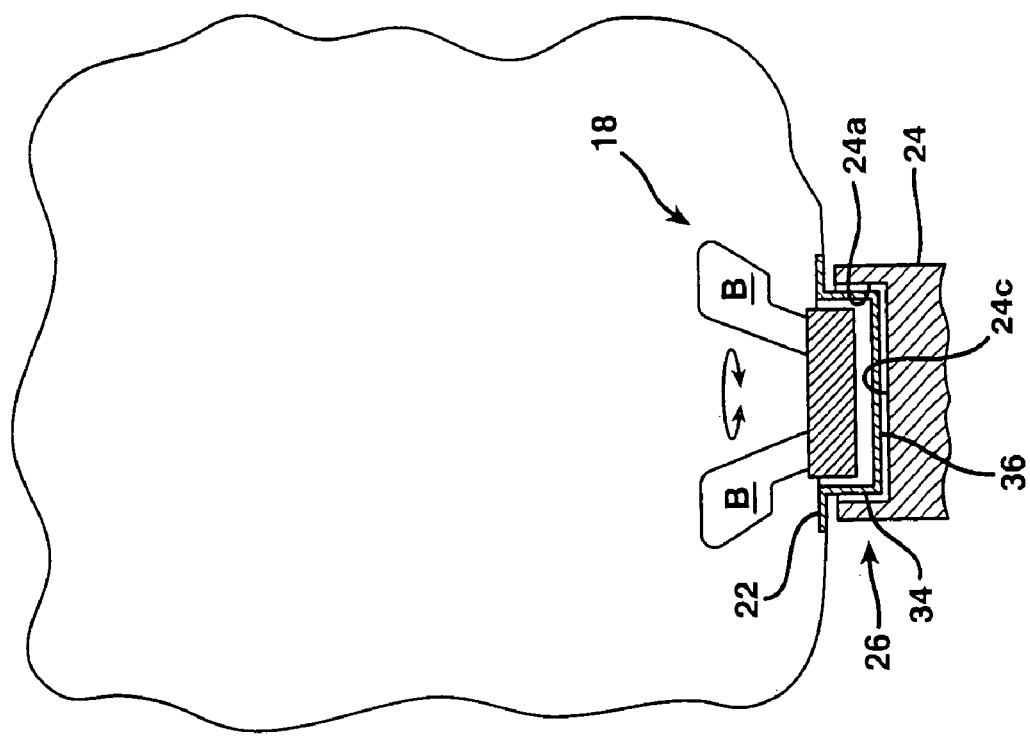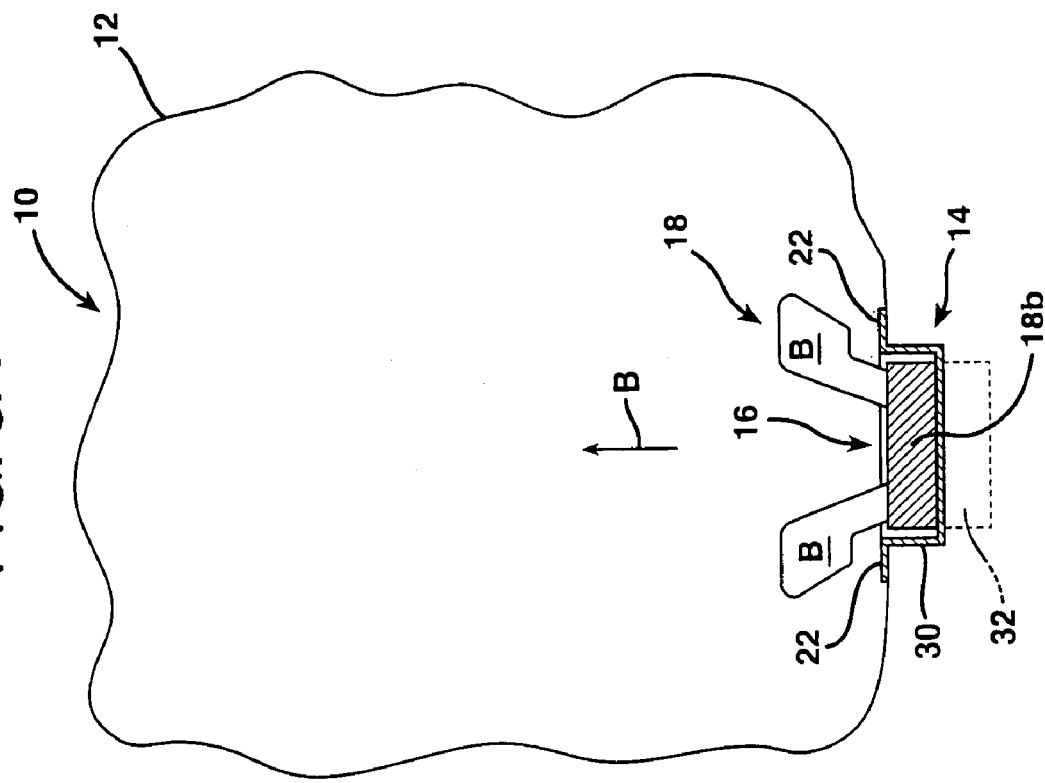

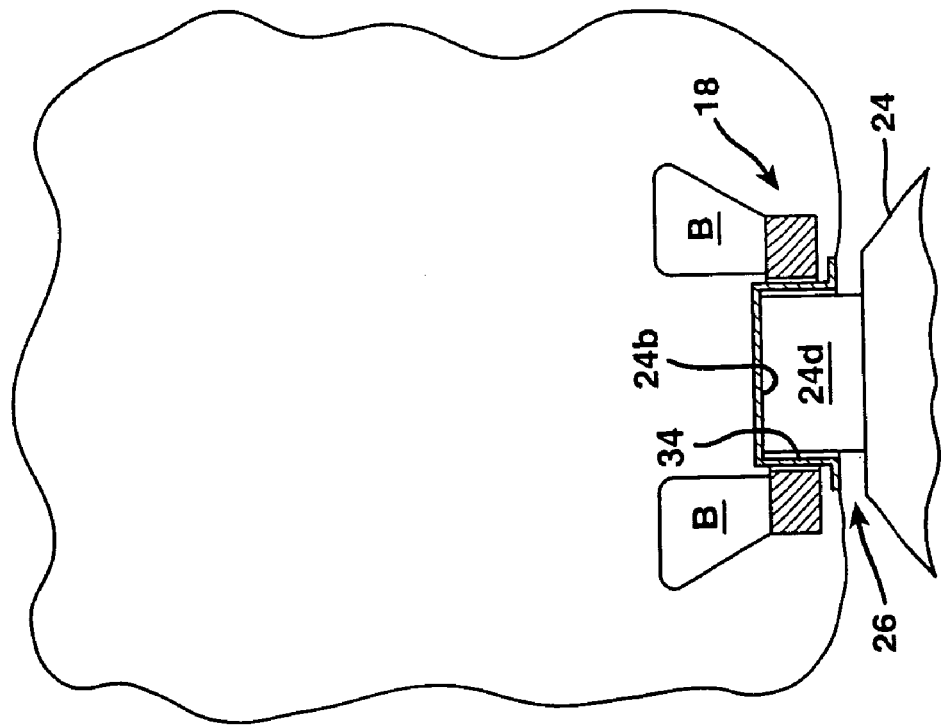
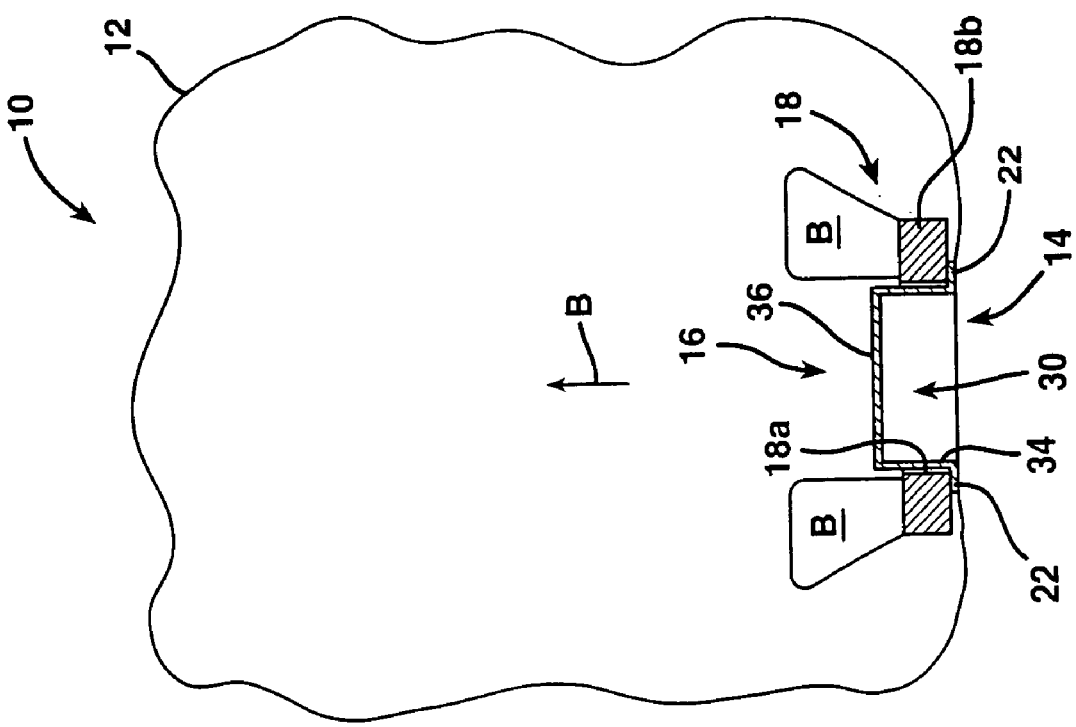

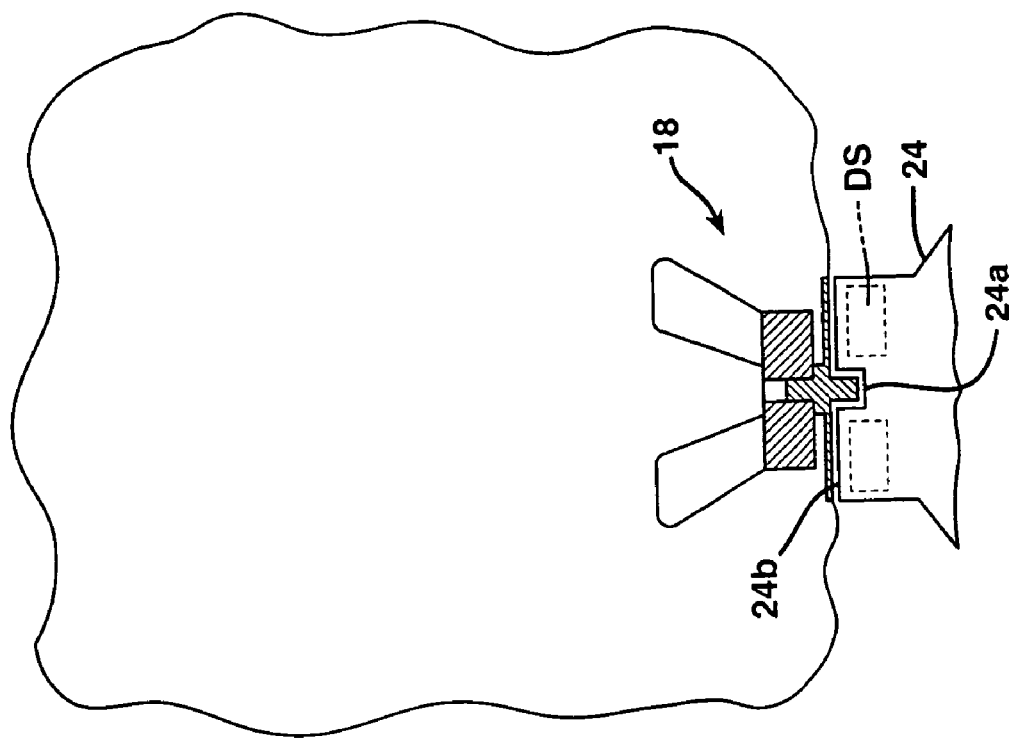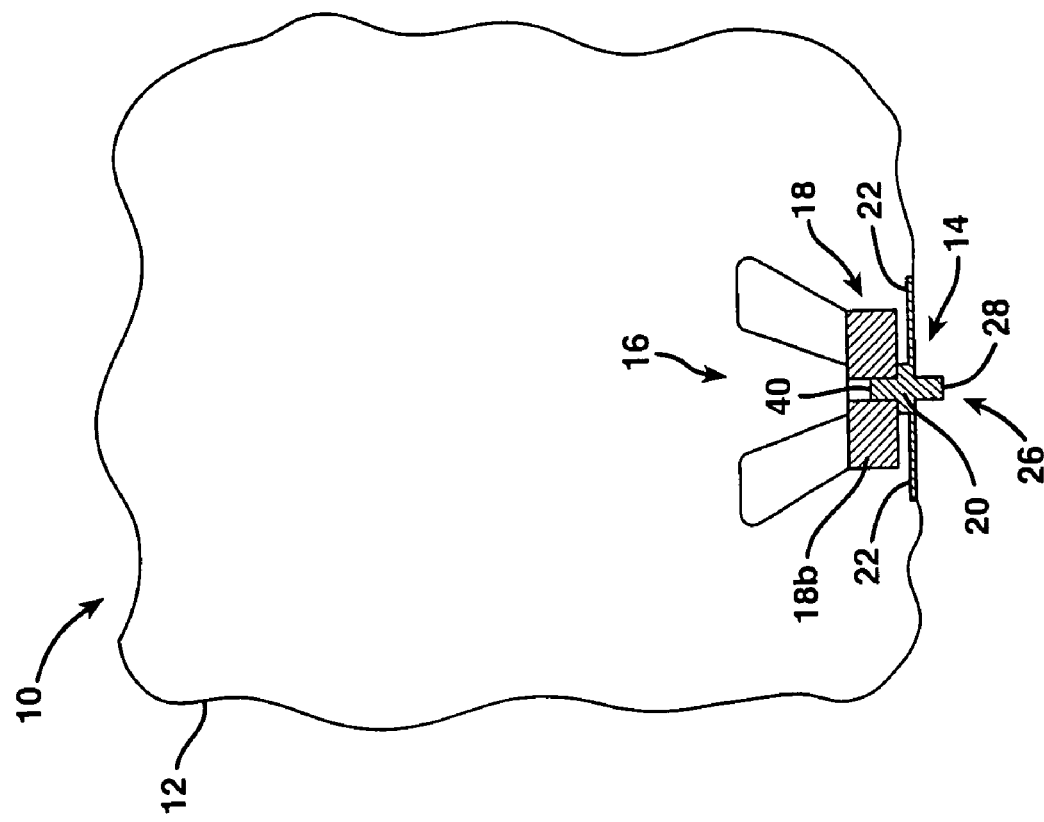

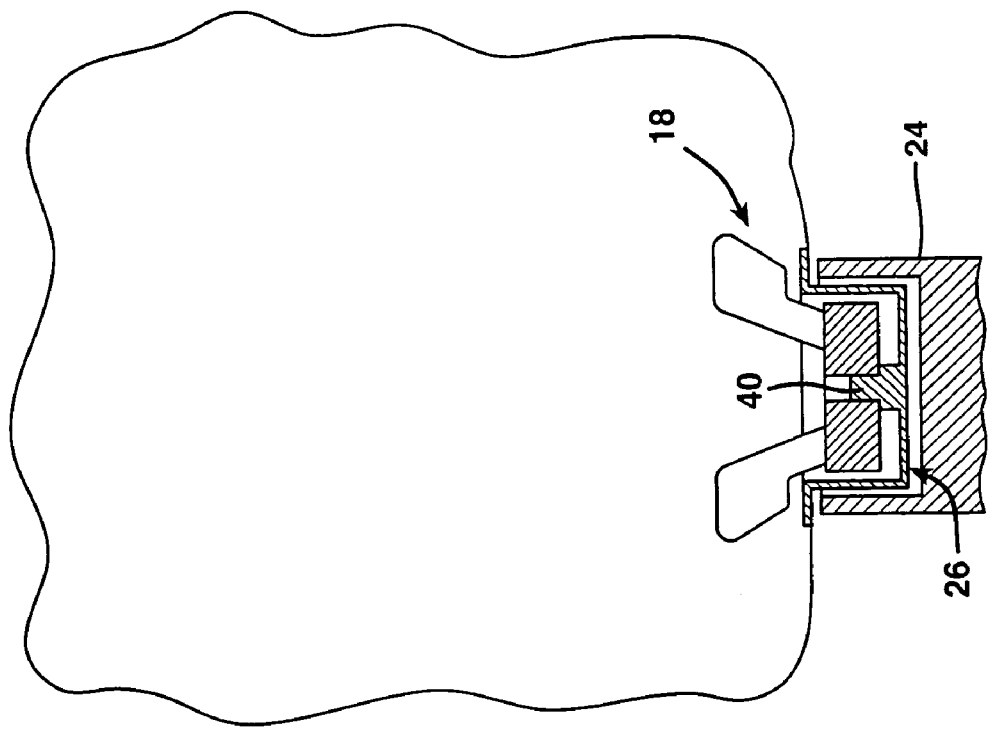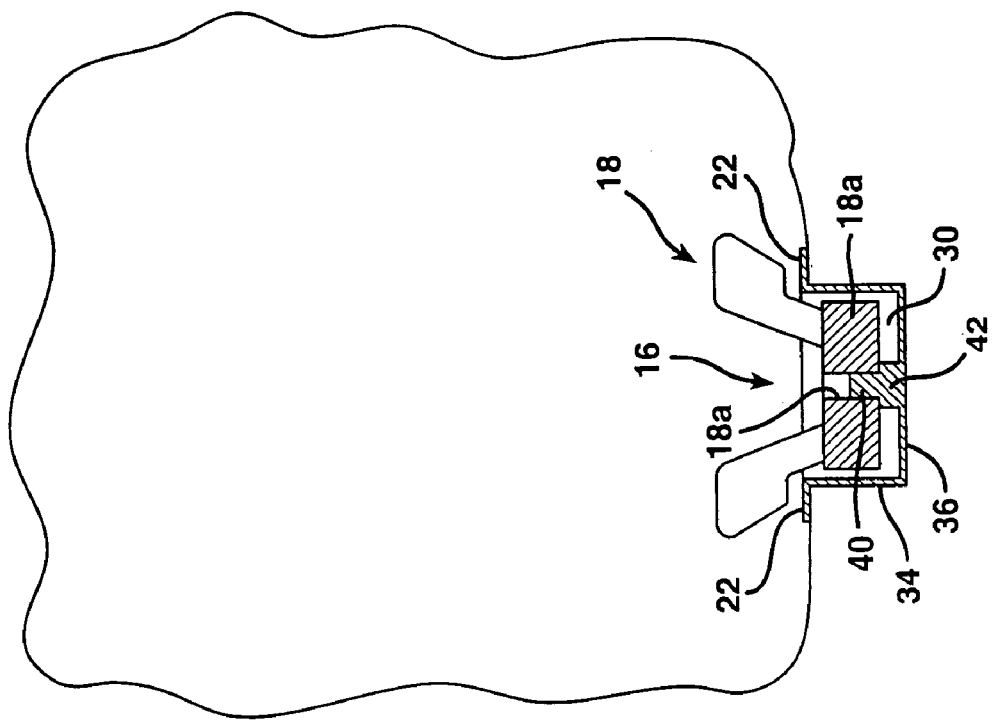

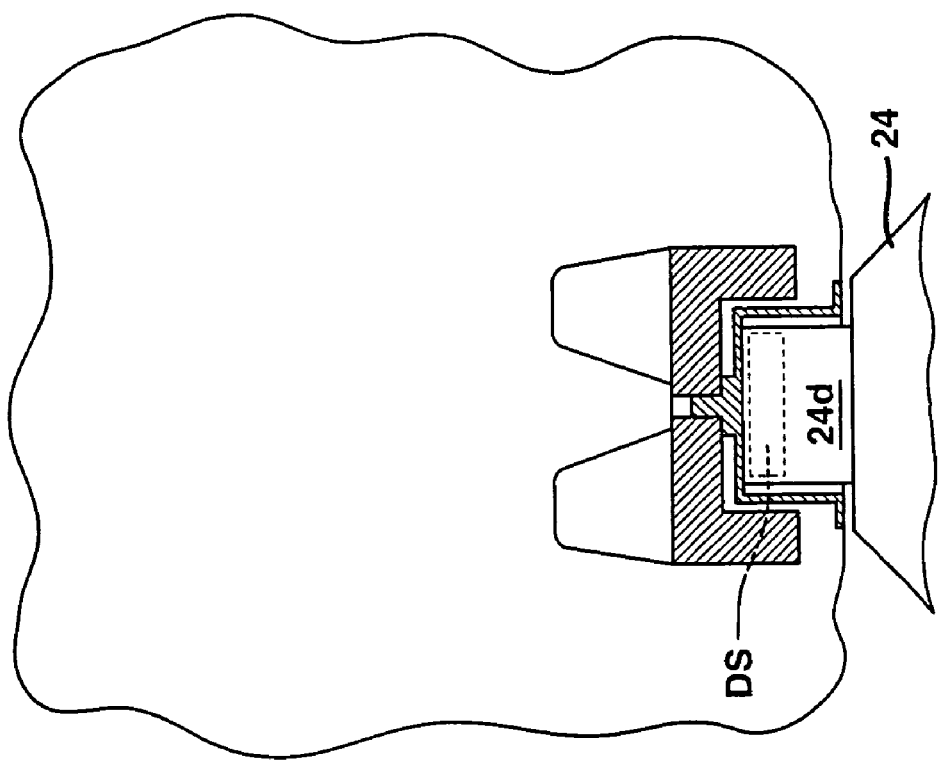
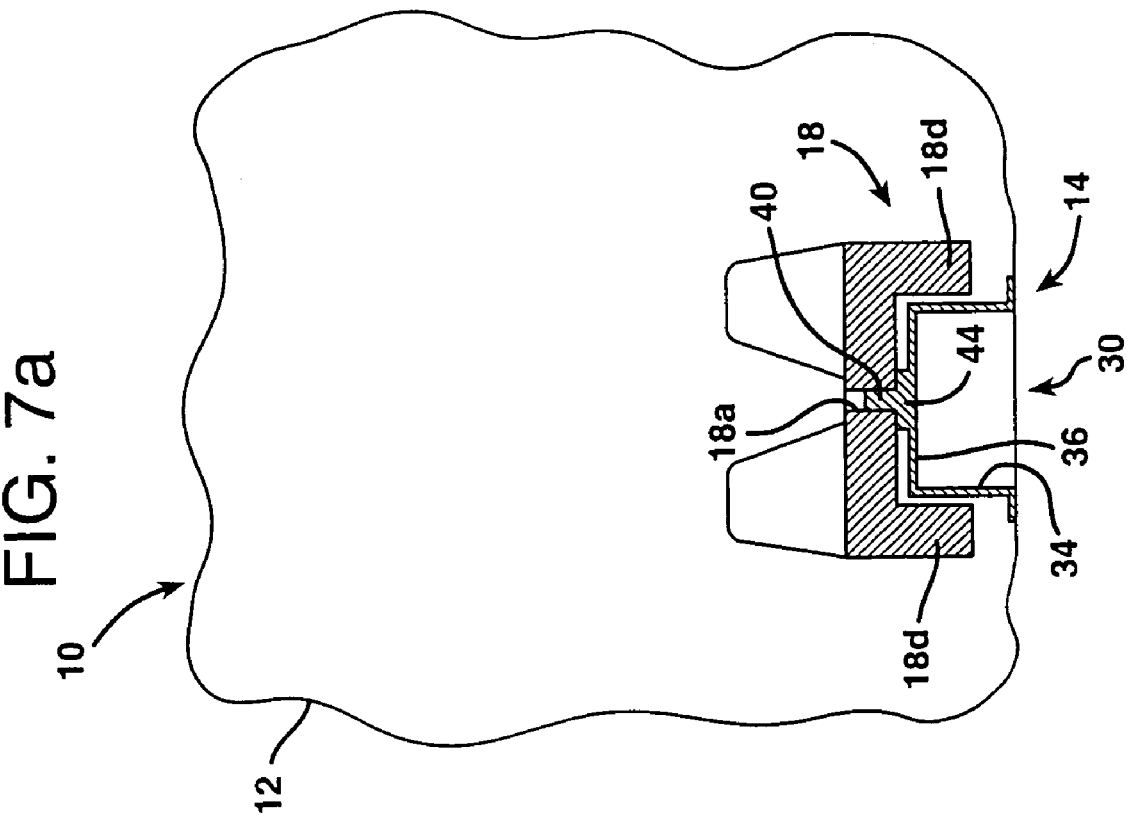

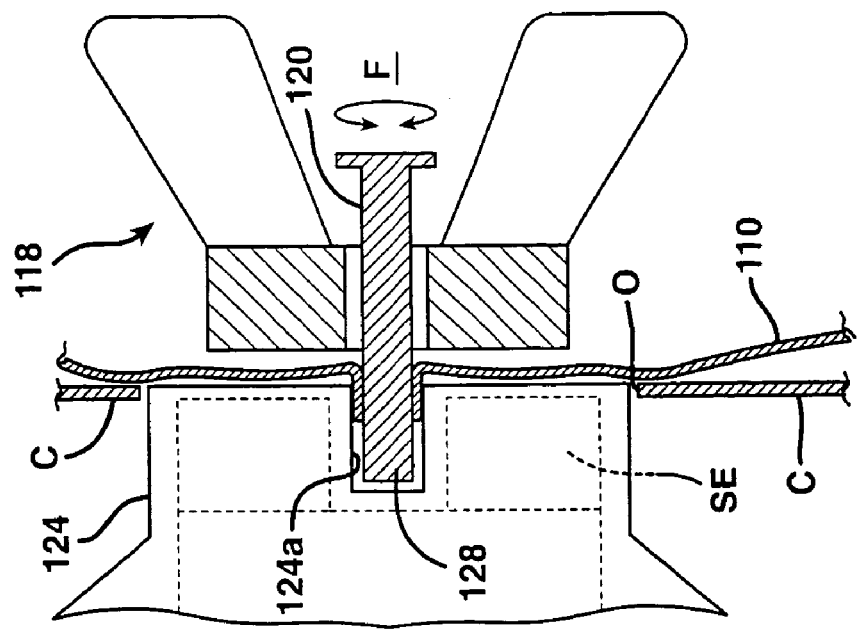
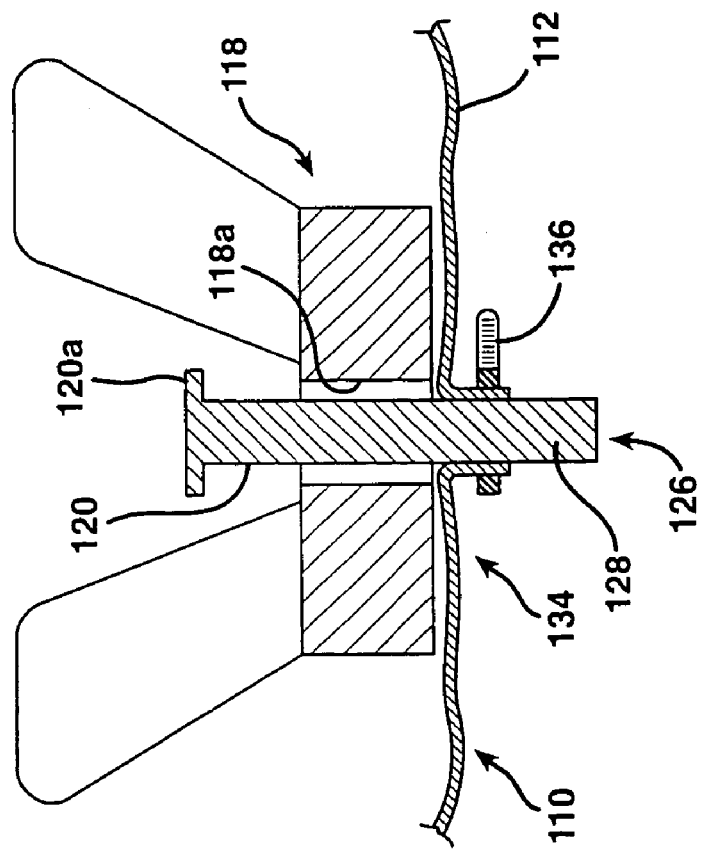

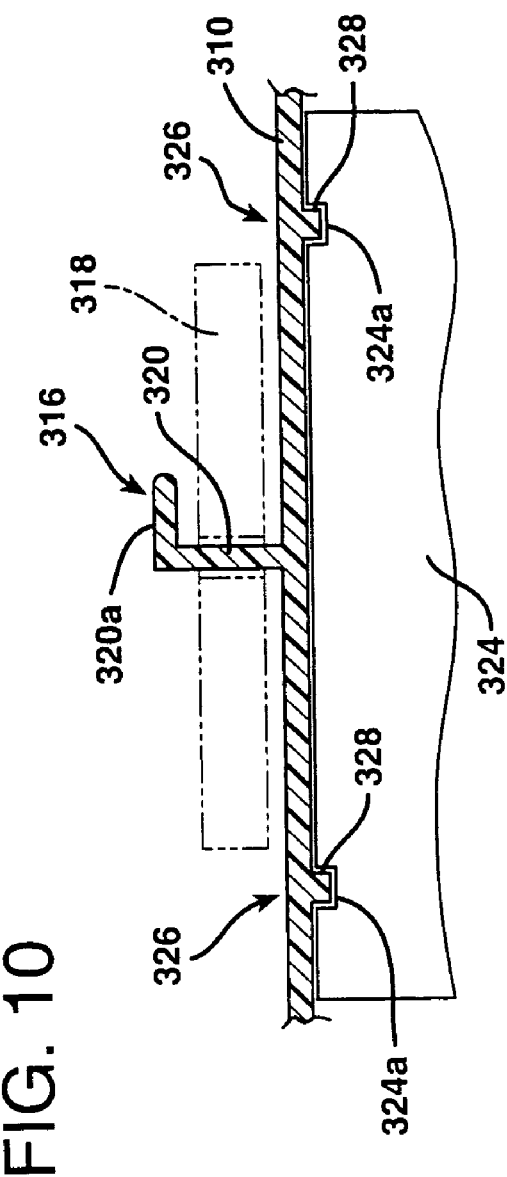
FIG. 10
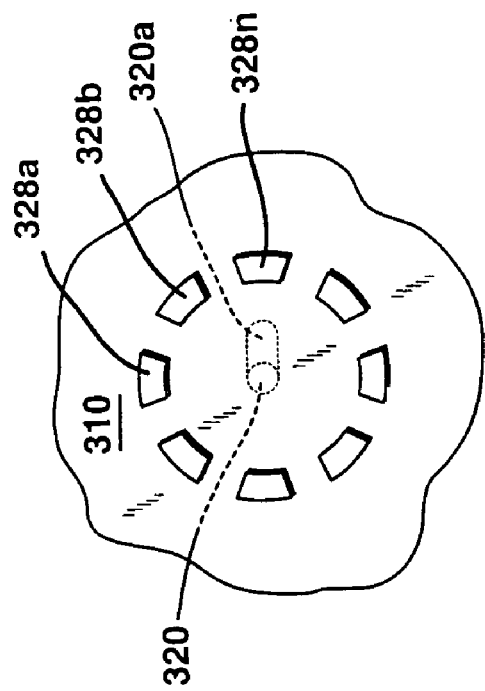
FIG. 10b
FIG. 10a

MIXING VESSEL WITH A FLUID-AGITATING ELEMENT SUPPORTED BY A ROLLER BEARING

This application claims the benefit of U.S. Provisional Patent Application Ser. No. 60/634,664, filed Dec. 9, 2004, and is a continuation-in-part of U.S. patent application Ser. No. 10/491,512, filed Apr. 1, 2004 now U.S. Pat. No. 7,481,572 the disclosures of which are incorporated herein by reference. This application is a continuation-in-part of Ser. No. 10/398,946, now U.S. Pat. No. 7,086,778, which is the national stage of PCT/US01/31459, filed Oct. 9, 2001, which claims the benefit of the following U.S. Provisional Patent Applications: (a) Ser. No. 60/239,187, filed Oct. 9, 2000; (b) Ser. No. 60/282,927, filed Apr. 10, 2001; and (c) Ser. No. 60/318,579, filed Sep. 11, 2001.

TECHNICAL FIELD

The present invention relates generally to vessels in which fluids are agitated and, more particularly, to a collapsible mixing vessel, or bag, including a fluid-agitating element supported by a roller bearing.

BACKGROUND OF THE INVENTION

Most pharmaceutical solutions and suspensions manufactured on an industrial scale require highly controlled, thorough mixing to achieve a satisfactory yield and ensure a uniform distribution of ingredients in the final product. Agitator tanks are frequently used to complete the mixing process, but a better degree of mixing is normally achieved by using a mechanical stirrer or impeller (e.g., a set of mixing blades attached to a metal rod). Typically, the mechanical stirrer or impeller is simply lowered into the fluid through an opening in the top of the vessel and rotated by an external motor to create the desired mixing action.

One significant limitation or shortcoming of such an arrangement is the danger of contamination or leakage during mixing. The rod carrying the mixing blades or impeller is typically introduced into the vessel through a dynamic seal or bearing. This opening provides an opportunity for bacteria or other contaminants to enter, which of course can lead to the degradation of the product. A corresponding danger of environmental contamination exists in applications involving hazardous or toxic fluids, or suspensions of pathogenic organisms, since dynamic seals or bearings are prone to leakage. Cleanup and sterilization are also made difficult by the dynamic bearings or seals, since these structures typically include folds and crevices that are difficult to reach. Since these problems are faced by all manufacturers of sterile solutions, pharmaceuticals, or the like, the U.S. Food and Drug Administration (FDA) has consequently promulgated strict processing requirements for such fluids, and especially those slated for intravenous use.

In an effort to overcome these problems, others have proposed alternative mixing technologies. Perhaps the most common proposal for stirring a fluid under sterile conditions is to use a rotating, permanent magnet bar covered by an inert layer of TEFLON, glass, or the like. The magnetic "stirrer" bar is placed on the bottom of the agitator vessel and rotated by a driving magnet positioned external to the vessel. An example of such an arrangement where the vessel is not a flexible bag is shown in U.S. Pat. No. 5,947,703 to Nojiri et al., the disclosure of which is incorporated herein by reference.

Of course, the use of such an externally driven magnetic bar avoids the need for a dynamic bearing, seal or other opening in the vessel to transfer the rotational force from the driving magnet to the stirring magnet. Therefore, a completely enclosed system is provided. This of course prevents leakage and the potential for contamination created by hazardous materials (e.g., cytotoxic agents, solvents with low flash points, blood products, etc.), eases clean up, and allows for the desirable sterile interior environment to be maintained, all of which are considered significant advantages.

Despite the advantages of this type of mixing systems and others where the need for a shaft penetrating into the vessel or dynamic seal is eliminated, a substantial, but heretofore unsolved problem with such systems is the difficulty in coupling a fluid-agitating element with an external motive device providing the rotation and/or levitation force. For example, when a vessel in the form of a flexible bag containing an unconfined fluid-agitating element is positioned in proximity to the motive device, the relative location of the fluid-agitating element is generally unknown. In the case of a small (10 liter or less) transparent bag, it is possible to manipulate the bag relative to the motive device in an effort to ensure that the fluid-agitating element is "picked up" and the desired coupling is formed. However, this is considered inconvenient and time consuming, especially if fluid is already present in the bag. Moreover, in the case where the bag is relatively large (e.g., capable of holding 100 liters or more) or formed of an opaque material, achieving the proper positioning of the fluid-agitating element relative to the external motive device is at a minimum difficult, and in many cases, impossible. In the absence of fortuity, a significant amount of time and effort is required to lift and blindly reposition the bag relative to the motive device, without ever truly knowing that the coupling is properly formed. Also, even if the coupling is initially formed, the fluid-agitating element may become accidentally decoupled or disconnected from the motive device during the mixing operation. In view of the semi-chaotic nature of such an event, the ultimate resting place of the fluid-agitating element is unknown and, in cases where the fluid is opaque (e.g., blood) or cloudy (e.g., cell suspensions), not easily determined. If the coupling ultimately cannot be established in the proper fashion, the desired fluid agitation cannot be achieved in a satisfactory manner, which essentially renders the set up useless. These shortcomings may significantly detract from the attractiveness of such fluid agitation systems from a practical standpoint.

In many past mixing arrangements, a rigid vessel is used with a fluid-agitating element directly supported by a post carrying a roller bearing, with the rotational force being supplied by an external device (see, e.g., U.S. Pat. No. 4,209,259 to Rains et al., the disclosure of which is incorporated herein by reference). While this direct support arrangement prevents the fluid-agitating element from becoming lost in the event of an accidental decoupling, the use of such post or like structure in a bag for receiving and holding a fluid-agitating element has not been proposed. The primary reason for this is that, in a typical flexible bag, neither the sidewalls nor any other structure is capable of providing the direct support for the fluid-agitating element or a corresponding bearing.

Thus, a need is identified for an improved manner of ensuring that the desired low friction support is provided for a fluid-agitating element in a vessel, such as a bag, rotated by an external motive device. The improvement provided by the invention would be easy to implement using existing manufacturing techniques and without significant additional expense. Overall, a substantial gain in efficiency and ease of use would be realized as a result of the improvement, and would greatly expand the potential applications for which advanced mixing systems may be used.

SUMMARY OF THE INVENTION

In accordance with one aspect of the invention, an apparatus intended for receiving a fluid and a rotatable fluid-agitating element is disclosed. The apparatus comprises a collapsible container or vessel, such as a flexible bag, capable of receiving and holding the fluid. A roller bearing provides low-friction support for the fluid-agitating element in the vessel.

In one embodiment, the vessel includes an inwardly projecting post. Preferably, the roller bearing includes an opening for receiving the post. The post may also retain and support the roller bearing.

The roller bearing may be attached to the post. In one alternative embodiment, the vessel includes a cap-shaped receiver for receiving the fluid-agitating element that projects toward an interior compartment of the bag, thereby forming an external cavity. In another alternative embodiment, the receiver is cup-shaped and forms a cavity in communication with the interior compartment of the collapsible vessel for at least partially receiving the roller bearing and the fluid-agitating element.

In accordance with a second aspect of the invention, an apparatus intended for receiving and mixing a fluid is disclosed. The apparatus comprises a magnetic fluid-agitating element and a collapsible vessel capable of receiving and holding the fluid. A roller bearing associated with the vessel provides low-friction support for the fluid-agitating element.

In one embodiment, the vessel includes a post and the roller bearing includes an opening for receiving the post. Preferably, the fluid-agitating element also includes an opening for receiving the post. Still more preferably, the post retains the fluid-agitating element and roller bearing on the post.

The roller bearing is preferably a ball bearing. In such case, the ball bearing may be attached to a rigid receiver forming part of the vessel. In any case, the roller bearing may also be attached to the fluid-agitating element to provide the desired low friction support.

Also disclosed as an aspect of the invention is a method of forming an assembly for agitating a fluid. The method comprises the steps of providing a flexible bag for receiving a magnetic fluid-agitating element, and supporting the fluid-agitating element on a roller bearing.

Preferably, the vessel includes a post and the bearing is a ball bearing including an opening. In such case, the supporting step may comprise placing the post through the opening. The method may further comprise the step of attaching the roller bearing to the post.

In one embodiment, the vessel includes a cap-shaped receiver for the fluid-agitating element and includes a sidewall. In such case, the method further comprises positioning the sidewall through an opening in the roller bearing. In another embodiment, the vessel includes a cup-shaped receiver with a cavity in communication with an interior compartment of the bag. In such case, the method includes the step of positioning the roller bearing in the cavity.

BRIEF DESCRIPTION OF THE DRAWINGS

FIG. 1a is a partially schematic, partially cross-sectional, enlarged cutaway side view of the rigid portion of the vessel in the embodiment of FIG. 1;

FIG. 1b is a partially schematic, partially cross-sectional, enlarged cutaway side view of the fluid-agitating element in the embodiment of FIG. 1;

FIG. 1c is an enlarged partially cutaway side view showing one possible manner of attaching a first receiver in the form of a post to the rigid portion of the vessel;

FIG. 3a is partially schematic, partially cross-sectional side view showing another embodiment of the vessel, including a hat or cap-shaped rigid portion having a cavity facing inwardly;

FIG. 3b is a side view similar to FIG. 3a;

FIG. 4a is partially schematic, partially cross-sectional side view showing another embodiment of the vessel, including a hat or cap-shaped rigid portion having a cavity facing outwardly;

FIG. 4b is a side view similar to FIG. 4a;

FIGS. 5a, 5b, 6a, 6b, and 7a, 7b are each partially schematic, partially cross-sectional side views of a vessel with a rigid portion for aligning a fluid-agitating element with a external structure, wherein the fluid-agitating element is directly supported by a slide bearing;

FIGS. 8a and 8b are enlarged, partially cross-sectional, partially cutaway side views of yet another embodiment of the vessel of the present invention;

FIG. 10 is an enlarged, partially cross-sectional, partially cutaway side view of still another embodiment of the vessel of the present invention;

FIGS. 10a and 10b are cutaway bottom views of the vessel of FIG. 10 showing two different embodiments;

DETAILED DESCRIPTION OF THE INVENTION

Figure 1:
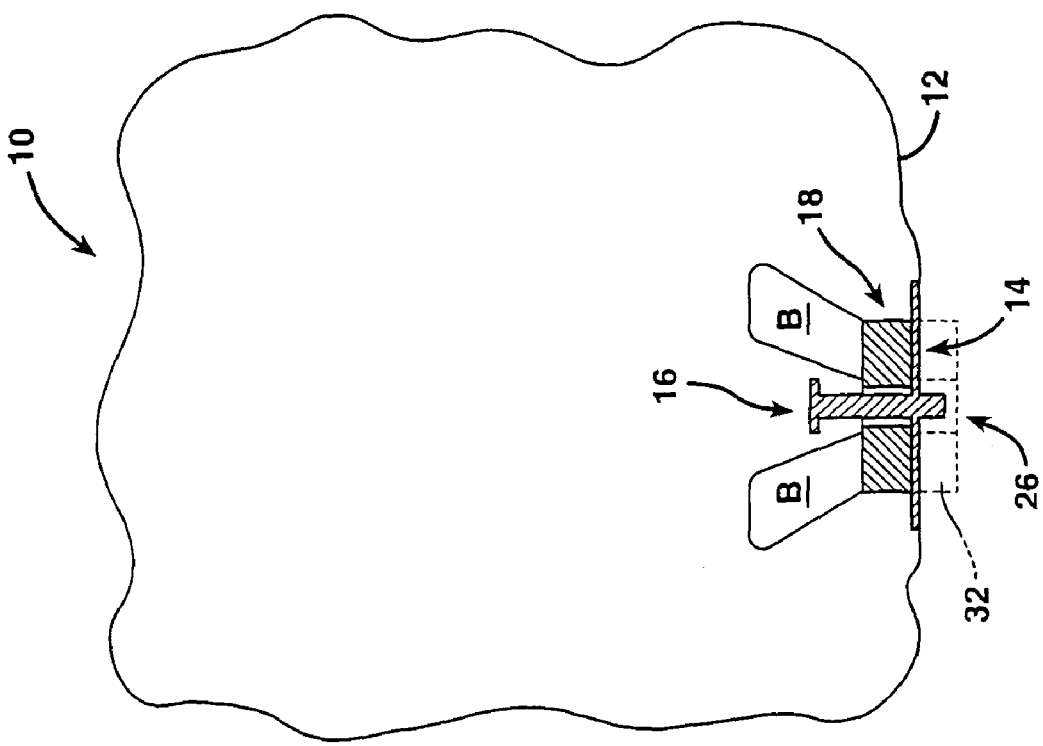
FIG. 1 is a partially schematic, partially cross-sectional side view of one embodiment of the present invention including a vessel in the form of a bag having a flexible portion and a rigid portion.

Reference is now made to FIG. 1, which discloses one embodiment of the vessel of the present invention in the form of a bag 10, which of course is collapsible when empty. In this embodiment, the bag 10 includes a body having a flexible or non-rigid portion 12, which is illustrated schematically, and a rigid or stiff portion 14, which is shown in cross-section. The bag 10 may be hermetically sealed and may have one or more openings or fittings (not shown) for introducing or recovering a fluid. Alternatively, the bag 10 may be unsealed or open-ended. The particular geometry of the bag 10 employed normally depends on the application and is not considered critical to the invention. For example, in the case of a sterile fluid, a hermetically sealed, pre-sterilized bag with an aseptic fitting might be desirable; whereas, in the case where sterility is not important, an open-ended or unsealed bag might be suitable. The main important point is that the bag 10 is capable of receiving and at least temporarily holding a fluid (which is used herein to denote any substance capable of flowing, as may include liquids, liquid suspensions, gases, gaseous suspensions, or the like, without limitation).

The rigid portion 14 includes a first receiver 16 for receiving and holding a fluid-agitating element 18 at a home location (or expected position), when positioned in the bag 10. It is noted that "holding" as used herein defines both the case where the fluid-agitating element 18 is directly held and supported by the first receiver 16 (see below) against any significant side-to-side movement (save tolerances), as well as where the first receiver 16 merely limits the fluid-agitating element to a certain degree of side-to-side movement within the bag 10. In this embodiment, an opening 18a is provided in the fluid-agitating element 18 and the first receiver 16 is a post 20 projecting toward the interior of the bag 10 (see FIGS. 1a and 1b). The post 20 is sized for receiving the fluid-agitating element 18 by extending through the opening 18a formed in the body 18b thereof (which is depicted as being annular, but not necessarily circular in cross-section). As illustrated in FIG. 1, it is preferable that the size of the opening 18a is such that the fluid-agitating element 18 may freely rotate and move in the axial direction along the post 20 without contacting the outer surface thereof. Despite this freedom of movement, the post 20 serving as the first receiver 16 is still considered to hold, confine, or keep the fluid-agitating element 18 at a home location or expected position within the vessel 20 by contacting the surface adjacent to the opening 18a as a result of any side-to-side movement (the boundaries of which are defined by the dimensions of the opening).

The flexible portion 12 of the bag 10 may be made of thin (e.g., having a thickness of between 0.1 and 0.2 millimeters) polyethylene film. The film is preferably clear or translucent, although the use of opaque or colored films is also possible. The rigid portion 14 including the post 20 may be formed of plastic materials, such as high density polyethylene (HDPE), ultrahigh molecular weight (UHMW) polyethylene, or like materials. Of course, these materials do have some inherent flexibility when used to form relatively thin components or when a moderate amount of bending force is applied thereto. Despite this flexibility, the rigid portion 14 is distinguished from the flexible portion 12, in that it generally maintains its shape under the weight of any fluid introduced in the bag 10.

Optionally, the post 20 may include a portion 20a for capturing the fluid-agitating element 18 and assisting in holding it thereon. The portion 20a is preferably oversized and forms the head or end of the post 20. By "oversized," it is meant that at least one dimension (length, width, diameter) of this portion 20a of the post 20 is greater than the corresponding dimension of the opening 18a in the fluid-agitating element 18. For example, the portion 20a is shown in FIG. 1 as being disc-shaped, such that it provides the head end of the post 20 with a generally T-shaped cross section. To prevent interference with the levitation and rotation of the fluid-agitating element 18, the oversized portion 20a is strategically positioned at a certain distance along the post 20. In the case where it is oversized, the post 20 may be removably attached to the rigid portion 14 through the opening 18a in the fluid-agitating element 18 (such as by providing a threaded bore in the rigid portion for receiving a threaded end of the post, or as shown in FIG. 1c, a bore 14a having a groove 14b for establishing a snap-fit engagement with a corresponding projection 20b on a tapered end portion 20c of the post). In the case where the post 20 is unitarily formed with the rigid portion 14 and includes an oversized head portion 20a, this portion should be sufficiently thin such that it flexes or temporarily deforms to allow the fluid-agitating element 18 to pass initially (see FIG. 1b and note action arrow A, which demonstrates the direction of force for deforming the oversized head 20a such that it passes through the opening 18a).

Alternatively, this portion 20a of the post 20 need not be oversized, as defined above, but instead may simply be sufficiently close in size to that of the opening 18a such that the fluid-agitating element 18 must be precisely aligned and register with the post 20 in order to be received or removed. In any case, it is again important to note that the fluid-agitating element 18 is held in place in the vicinity of the post 20, but remains free of direct attachment. In other words, while the first receiver 16 (post 20) confines or holds the fluid-agitating element 18 at a home location or expected position within the bag 10, it is still free to move side-to-side to some degree (which in this case is defined by the size of the opening 18a), and to move along the first receiver 16 in the axial direction (vertical, in the embodiment shown in FIG. 1), as is necessary for levitation.

Figure 16A:
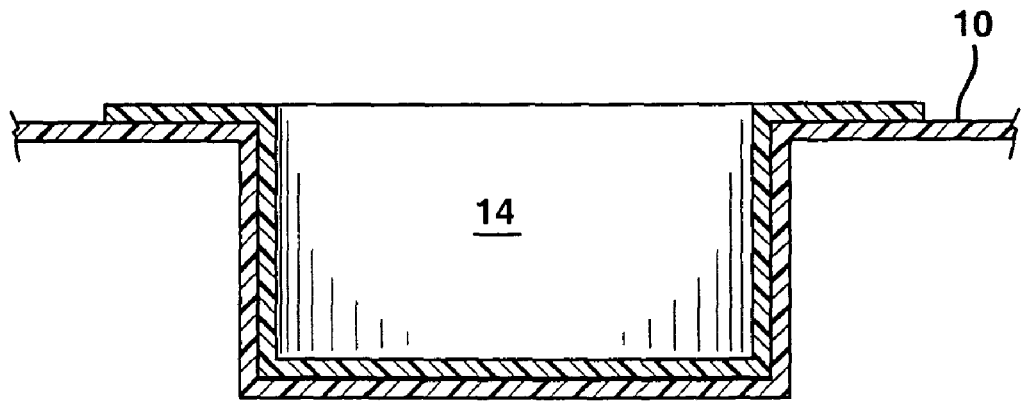
FIGS. 16a and 16b are enlarged, cross-sectional cutaway side views showing two different ways in which the rigid receiver may be connected to the bag forming the vessel.
Figure 16B:
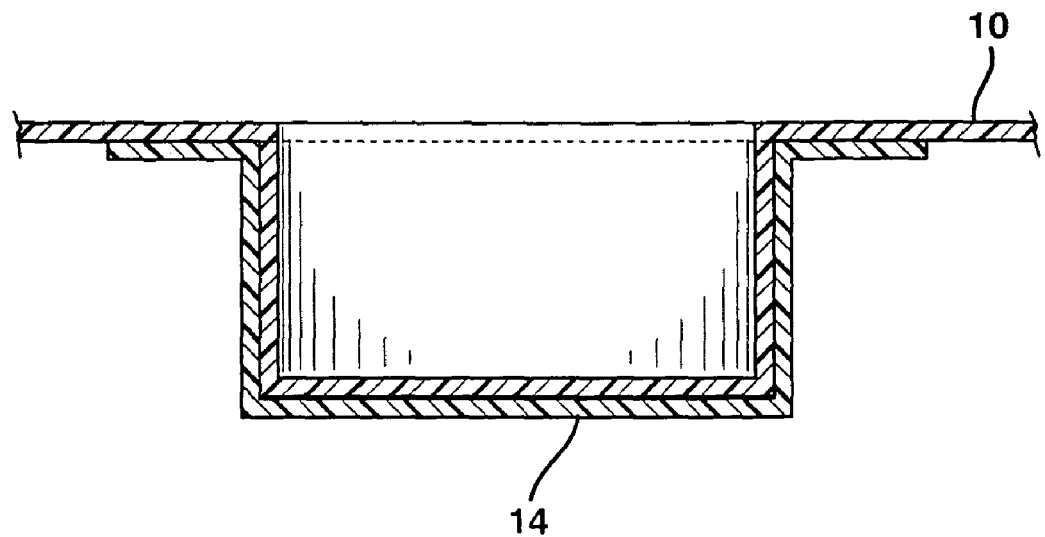

As perhaps best shown in FIG. 1a, the rigid portion 14 in this embodiment further includes a substantially planar peripheral flange 22. The flange 22 may be any shape or size, and is preferably attached or connected directly to the bag 10 at the interface I between the two structures (which may be created by overlapping the material forming the flexible portion 12 of the bag on an inside or outside surface of the flange 22 to form an overlapping joint, or possibly in some cases by forming a butt joint). In the case where the bag 10 and flange 22 are fabricated of compatible plastic materials, the connection may be made using well-known techniques, such as ultrasonic or thermal welding (heat or laser) at the interface to form a seal (which is at least liquid-impervious and preferably hermetic). Alternatively, other means of connection (e.g., adhesives), may be used at the interface I, although this is obviously less preferred in view of the desirability in most cases for the more reliable, leak-proof seal afforded using welding techniques. In either case, the judicious use of inert sealants maybe made along the joint thus formed to ensure that a leak-proof, hermetic seal results. As discussed further below, the need for such an interface may be altogether eliminated by simply affixing the rigid portion 14 to an inside or outside surface of the bag 10 (see FIGS. 16a and 16b).

As should be appreciated, the bag 10 shown in FIG. 1 may be manufactured as described above, with the fluid-agitating element 18 received on the post 20 (which may be accomplished using the techniques shown in FIGS. 1b and 1c). The empty bag 10 may then be sealed and folded for shipping, with the fluid-agitating element 18 held at the home location by the post 20. Holding in the axial direction (i.e., the vertical direction in FIG. 1) may be accomplished by folding the bag 10 over the post 20, or by providing the portion 20a that is oversized or very close in size to the opening 18a in the fluid-agitating element 18.

When ready for use, the bag 10 is then unfolded. It may then be placed in a rigid or semi-rigid support structure, such as a container C, partially open along at least one end such that at least the rigid portion 14 remains exposed (see FIG. 2). Fluid F may then be introduced into the bag 10, such as through an opening or fitting (which may be a sterile or aseptic fitting, in the case where the bag 10 is pre-sterilized or otherwise used in a sterile environment). As should be appreciated, in view of the flexible or non-rigid nature of the bag 10, it will generally occupy any adjacent space provided in an adjacent support structure or container C when a fluid F (liquid or gas under pressure) is introduced therein (see FIG. 2).

Figure 2:
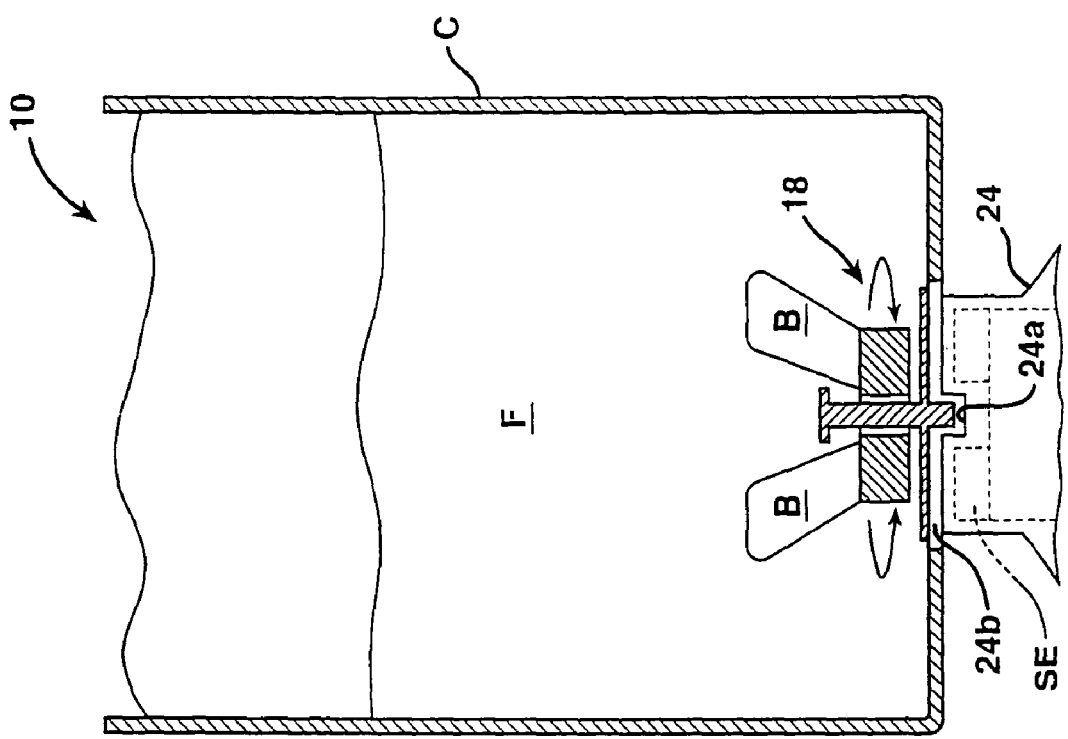
FIG. 2 is a partially schematic, partially cross-sectional side view showing the vessel of FIG. 1 positioned in a rigid vessel, with the fluid-agitating element aligned with and levitated/rotated by an adjacent motive device.

An external motive device 24 is then used to cause the fluid-agitating element 18 (which is at least partially magnetic or ferromagnetic) to at least rotate to agitate any fluid F in the bag 10. In the embodiment of FIG. 2, the fluid-agitating element 18 is at least partially magnetic and is shown as being levitated by the motive device 24, which is optional but desirable. As described in U.S. Pat. No. 6,416,215 (the disclosure of which is incorporated herein by reference), the levitation may be provided by a field-cooled, thermally isolated superconducting element SE (shown in phantom in FIG. 2) positioned within the motive device 24 and thermally linked to a cooling source (not shown). As also described therein, the fluid-agitating element 18 may then be rotated by rotating the superconducting element SE (in which case the fluid-agitating element 18 should produce an asymmetric magnetic field, such as by using at least two spaced magnets having alternating polarities). Another option is to use a separate drive structure (e.g., an electromagnetic coil) to form a coupling capable of transmitting torque to the particular fluid-agitating element (which may be "levitated" by a hydrodynamic bearing; see, e.g., U.S. Pat. No. 5,141,327 to Shiobara). While it is of course desirable to eliminate the need for a dynamic seal or opening in the bag through which a drive structure (such as a shaft) extends, the particular means used to levitate and/or rotate the fluid-agitating element 18 (which is preferably magnetic) is not considered critical to practicing the inventions disclosed herein.

The fluid-agitating element 18 is also depicted as including a plurality of vanes or blades B to improve the degree of fluid agitation. If present, the vanes or blades B preferably project in a direction opposite the corresponding surface of the rigid portion 14. The particular number, type, and form of the vanes or blades B is not considered important, as long as the desired degree of fluid agitation for the particular application is provided. Indeed, in applications where only gentle agitation is required, such as to prevent damage to delicate suspensions or to merely prevent stagnation of the fluid F in the bag 10, the vanes or blades B need not be provided, as a rotating smooth-walled annular element 18 still provides some degree of fluid agitation.

As explained above, it is important to not only know the general location or position of the fluid-agitating element 18 within the bag 10, but also to assure its position relative to the motive device 24. To do so, the rigid portion 14 may be provided with a second receiver 26 to facilitate the correct positioning of the motive device 24 relative to the fluid-agitating element 18 when held at the home location. In the embodiment shown in FIGS. 1a and 1b, the second receiver 26 takes the form of a second post 28 projecting in a direction opposite the first post 20. Preferably, the second post 28 is essentially coaxial with the first post 20 (although the post 20 may be a separate component that fits into a receiver 14a defined by the second post 28; see FIG. 1c) and is adapted to receive an opening 24a, such as a bore, in the adjacent end face 24b forming a part of the housing for the motive device 24. Consequently, the second post 28 helps to assure that the alignment between the fluid-agitating element 18 (which is generally held in the vicinity of the first receiver 16/post 20, which is the home location) and the motive device 14 is proper such that the desired coupling for transmitting the levitation or rotational force may be formed.

Preferably, the second receiver 26, such as second post 28, has a cross-sectional shape corresponding to the shape of the opening 24a. For example, the second post 28 may be square in cross-section for fitting in a correspondingly-shaped opening 24a or locator bore. Likewise, the second post 28 could have a triangular cross-sectional shape, in which case the opening 28 would be triangular. Myriad other shapes could also be used, as long as the shape of the second receiver 26 compliments that of the opening 24a such that it may be freely received therein. In this regard, it is noted that a system of matching receivers and openings may be used to ensure that the fluid-agitating element 18 in the bag 10 corresponds to a particular motive device 24. For example, in the case where the fluid-agitating element 18 includes a particular arrangement of magnets producing a magnetic field that corresponds to a particular superconducting element or drive structure, the second receiver 26 may be provided with a certain shape that corresponds only to the opening 24 in the motive device 24 having that type of superconducting element or drive structure. A similar result could also be achieved using the relative sizes of the second receiver 26 and the opening 24a, as well as by making the size of the opening 18a in the fluid-agitating element 18 such that it only fits on a first receiver 16 having a smaller width or diameter, and then making the second receiver 26 correspond only to a motive device opening 24a corresponding to that fluid-agitating element 18.

In many past arrangements where a rigid vessel is used with a fluid-agitating element directly supported by a bearing, an external structure is provided to which a motive device could be directly or indirectly attached and held in a suspended fashion This structure serves to automatically align the motive device with the fluid-agitating element supported therein. However, a bag 10 per se is generally incapable of providing reliable support for the motive device 24, which can weigh as much as twenty kilograms. Thus, the motive device 24 in the embodiments disclosed herein for use with a vessel in the form of a bag 10 is generally supported from a stable support structure (not shown), such as the floor, a wheeled, height adjustable platform, or the like. Since there is thus no direct attachment with the bag 10, the function performed by the second receiver 26 in aligning this device with the fluid-agitating element 18 is an important one.

Another embodiment of the vessel is shown in FIGS. 3a and 3b. In this embodiment, the vessel is again a bag 10 including a flexible portion 12 and a rigid portion 14. The rigid portion 14 is cap or hat-shaped with a peripheral flange 22 for attachment to the flexible portion 12 of the bag 10. The connection between the two structures may be formed using the various techniques described above, and preferably results in a fluid-impervious, hermetic seal. The rigid portion 14 includes a first receiver 16 in the form of a recess or cavity 30 facing the interior of the bag (see action arrow B) for receiving a correspondingly-shaped portion of the fluid-agitating element 18 in the bag 10 and holding it at a home location, at least when oriented as shown in FIG. 3a. The portion of the fluid-agitating element 18 received in the cavity 30 is preferably the body 18b, which as described above is at least partially magnetic or ferromagnetic and may optionally support a plurality of vanes or blades B. Preferably, the body 18b of the fluid-agitating element 18 is circular in cross-section and the cavity 30 is sized and shaped such that the body (which need not include opening 18a in view of the absence of post 20) may freely be inserted, rotate, and levitate therein. However, as with the first embodiment, the fluid-agitating element 18 could also be in the form of a conventional magnetic stirrer (which of course would not be levitated), such as a bar having a major dimension less than the corresponding dimension (e.g., the diameter) of the cavity 30. In any case, the fluid-agitating element 18 in this embodiment is again free of direct attachment from the first receiver 16, but is held at a home location, even in the event of accidental decoupling.

Thus, in the manner similar to that described above with respect to the first embodiment, the fluid-agitating element 18 may be positioned in the first receiver 16 in the bag 10. The bag 10 may then be sealed, folded for storage or shipping, stored or shipped, and ultimately unfolded for use. The folding is preferably completed such that the fluid-agitating element 18 is captured in the cavity 30 and remains held in place during shipping by an adjacent portion of the bag 10. Consequently, upon unfolding the bag 10, the fluid-agitating element 18 is at the expected or home location, but remains free of direct attachment and ready to be rotated (and possibly levitated). If levitated, the levitation height established by the superconducting bearing or hydrodynamic bearing is preferably such that at least a portion of the body 18b of the fluid-agitating element 18 remains within the confines of the cavity 30. This helps to assure that the fluid-agitating element 18 remains held at the home location (that is, in the vicinity of the first receiver 16), even in the case of accidental decoupling from the motive device 24. In other words, in the event of an accidental decoupling, the fluid-agitating element 18 will engage the sidewall of the cavity 30 and simply come to rest therein, which defines the home location. This not only improves the chance of an automatic recoupling, but also makes the task of manually reforming the coupling an easy one.

An option to assure that a magnetic fluid-agitating element 18 remains associated with the first receiver 16, even if inverted, is to attach an attractive structure, such as a magnet 32 (shown in phantom in FIG. 3a), to the exterior of the rigid portion 14. The non-contact coupling thus established helps ensure that the fluid-agitating element 18 remains in the home location prior to being coupled to an external motive device. The magnet 32 is removed once the bag 10 is positioned on or in a support structure, such as a container C (see FIG. 2). Such a magnet 32 may also be used with the embodiment of FIG. 1, which eliminates the need for providing the post 20 with portion 20a. The magnet 32 is preferably annular with an opening that is received by the second receiver 26, which advantageously helps to ensure that the alignment is proper for forming the coupling.

Yet another option is to provide a frangible adhesive on the fluid-agitating element 18 to hold it in place temporarily in the first receiver 16 prior to use. The strength of any adhesive used is preferably such that the bond is easily broken when the fluid-agitating element 18 is levitated in the first receiver 16. Of course, the use of such an adhesive might not be possible in situations where strict regulations govern the purity of the fluid being mixed.

With reference to FIG. 3b, the first receiver 16 in this embodiment also serves the dual function of helping to align the fluid-agitating element 18 relative to an external motive device 24. Specifically, the periphery of the sidewall 34 and the end wall 36 defining the cavity 30 in the rigid portion 14 define a second receiver 26 adapted to receive an opening 24a formed in an adjacent face of a motive device 24. As described above, the opening 24a is preferably sized and shaped for being received by the second receiver 26, and may even help to ensure that the bag 10 is used only with a motive device 24 having the correct superconducting element or magnetic structure(s) for levitating and/or rotating the fluid-agitating element 18. For example, in the case where the sidewall 34 and end wall 36 provide the second receiver 26 with a generally cylindrical shape, the opening 24a is also cylindrical. Preferably, the opening 24a also has a depth such that the end wall 36 rests on the corresponding face 24c of the motive device 24. This feature may be important to ensure that the gap between the superconducting element and/or drive structure in the motive device 24 and the at least partially magnetic or ferromagnetic body 18b of the fluid-agitating element 18 is minimized, which helps to ensure that the strongest possible coupling is established and that the maximum amount of driving torque is transferred. The gaps are shown as being oversized in FIG. 3b merely to provide a clear depiction of the relative interaction of the structures shown. However, in the case where the entire housing of the motive device 24 is rotated, it may be desirable to provide a certain amount of spacing between the sidewall 34, the end wall 36, and the corresponding surfaces defining the opening 24a to avoid creating any interference.

FIGS. 4a and 4b show an embodiment similar in some respects to the one shown in FIG. 3a and 3b. For example, the rigid portion 14 includes a peripheral flange 22 connected to the flexible portion 12 of the bag 10 to form a seal. Also, the rigid portion 14 includes a sidewall 34 and end wall 26 that together define a cavity 30. However, a major difference is that the cavity 30 of the rigid portion 14 essentially faces outwardly, or toward the exterior of the bag 10 (e.g., in a direction opposite action arrow B). Consequently, the sidewall 34 and end wall 36 define the first receiver 16 for receiving the fluid-agitating element 18, which is shown having an annular body 18b that is at least partially magnetic or ferromagnetic and may support a plurality of vanes or blades B. As should be appreciated, the first receiver 16 in the form of the periphery of the sidewall 34 provides a similar receiving function as both the post 20 and the cavity 30 of the other embodiments, since it is capable of maintaining, holding, or confining the fluid-agitating element 18 substantially in a home or expected position within the bag 10. The maximum amount of side-to-side movement is of course dependent on the size of the opening 18a in the fluid-agitating element.

Additionally, the outwardly-facing cavity 30 is adapted to serve as the second receiver 26 for receiving a portion of a motive device 24 used to levitate and rotate the fluid-agitating element 18 and serving to align the two. Specifically, the motive device 24 may include a head end 24d adapted for insertion in the cavity 30 to form the desired coupling with the fluid-agitating element 18 positioned adjacent thereto. As with the embodiments described above, the spacing between the head end 24d and at least the sidewall 34 is preferably minimized to maximize the strength of the coupling between the motive device 24 and the fluid-agitating element 18.

Moreover, in view of the rigid nature of the rigid portion 14, the end face 24b of the head end 24d may rest against and assist in supporting the bag 10 (which, as described above, may be positioned in a separate, semi-rigid container (not shown)).

In each of the above-referenced embodiments, the possible use of a levitating fluid-agitating element 18 with a superconducting bearing or a hydrodynamic bearing is described. In such systems, a real possibility exists that the fluid-agitating element 18 might accidentally decouple or disconnect from the motive device 24, such as if the fluid is viscous or the amount of torque transmitted exceeds the strength of the coupling. In a conventional bag, the process of reestablishing the coupling is extraordinarily difficult, since the location of the fluid-agitating element 18 within the bag 10 is unknown. In a sterile environment, opening the bag 10 and using an implement to reposition or "fish" out the fluid-agitating element 18 is simply not an option. Thus, an added advantage of the use of the first receiver 16 in each of the above-referenced embodiments is that, despite being free from direct attachment, it still serves the function of holding the fluid-agitating element 18 at the home location in instances where accidental decoupling occurs. This significantly reduces the downtime associated with such an event, since the general position of the fluid-agitating element 18 is known. The use of a first receiver in the bag 10 also improves the chances of automatic recoupling, since the fluid-agitating element 18 remains generally centered relative to the motive device 14 and held generally at the home location, even when decoupling occurs.

A related advantage is provided by forming the first receiver 16 in or on a rigid portion 14 of the bag 10. Specifically, in the case where a fluid-agitating element rests on a surface of a bag, the contact over time could result in damage and could even lead to an accidental perforation, which is deleterious for obvious reasons. The possibility for such damage or perforation also exists when a levitating fluid-agitating element 18 accidentally decouples. Advantageously, the potential for such damage or perforation is substantially eliminated in the foregoing embodiments, since the first receiver 16 helps to keep the fluid-agitating element 18 adjacent to the flange 22 of the rigid portion 14, which is generally thicker and less susceptible to being damaged or perforated. In other words, if the fluid-agitating element 18 becomes decoupled, it only engages or contacts the rigid portion 14 of the bag 10. Thus, it is preferable for the flange 22 to be oversized relative to the fluid-agitating element 18.

Up to this point, the focus has been on a fluid-agitating element 18 capable of levitating in the vessel. However, as briefly noted above, the inventions described herein may also be applied to a bag 10 in combination with a fluid-agitating element 18 directly supported by one or more bearings. For example, as shown in FIGS. 5a and 5b, the first receiver 16 associated with the rigid portion 14 of the bag 10 may be in the form of an inwardly-projecting post 20 including a slide bearing 40 for providing direct support for the fluid-agitating element 18. The bearing 40 is preferably sized and shaped such that it fits into an opening 18a forming in the fluid-agitating element 18, which may rest on the adjacent surface of the post 20 or may be elevated slightly above it. In either case, it should be appreciated that the first receiver 16 receives and holds the fluid-agitating element 18 in a home location, both during shipping and later use.

In view of the direct nature of the support, the material forming the slide bearing 40 is preferably highly wear-resistant with good tribological characteristics. The use of a slide bearing 40 is preferred in applications where the bag 10 is disposable and is merely discarded, since it is less expensive than a corresponding type of mechanical roller bearing (and is actually preferred even in the case where the bag 10 is reused, since it is easier to clean). However, it is within the broadest aspects of the invention to provide the first receiver 16 with a conventional roller bearing for providing direct, low-friction, rolling support for the rotating fluid-agitating element 18, although this increases the manufacturing expense and may not be acceptable in certain applications.

The rigid portion 14 of the bag 10 in this embodiment may further include a second receiver 26 in the form of a second post 28 coextensive and coaxial with the first post 20. The second post 28 is received in an opening 24a formed in an end face 24b of a motive device 24. In view of the direct support provided for the fluid-agitating element 18 by the bearing 40, the motive device 24 in this case includes only a drive structure DS (shown in phantom in FIG. 5b) for forming a coupling with the body 18b, which is magnetic or ferromagnetic (iron, magnetic steel, etc.). The drive structure DS may be a permanent magnet or may be ferromagnetic, as necessary for forming the coupling with the fluid-agitating element 18, which may be disc-shaped, cross-shaped, an elongated bar, or have any other suitable shape. The drive structure DS may be rotated by a direct connection with a motor (not shown), such as a variable speed electric motor, to induce rotation in the fluid-agitating element 18. Alternatively, the drive structure DS may be an electromagnet with windings to which current is supplied to cause the magnetic fluid-agitating element 18 rotate and possibly levitate slightly to create a hydrodynamic bearing (see, e.g., U.S. Pat. No. 5,141,327, the disclosure of which is incorporated herein by reference). Again, it is reiterated that the particular type of motive device 24 employed is not considered critical to the present invention.

FIGS. 6a and 6b show an embodiment of the bag 10 in which the first receiver 16 is in the form of a cavity 30 formed in the rigid portion 14 and facing inwardly. A bearing 40 is provided in the cavity 30 for providing direct support for a fluid-agitating element 18 positioned therein. As with the embodiment described immediately above, the bearing 40 may be a slide bearing adapted for insertion in the opening 18a of the fluid-agitating element 18 formed on the head end of a post 42. The post 42 may be supported by or unitarily formed with the end wall 36. Despite the depiction of a slide bearing 40, it is reiterated that the particular type of bearing used is not considered critical, as long as rotational support is provided for the fluid-agitating element 18 and the other needs of the particular fluid-agitating operation are met (e.g., low friction, reduced expense, easy clean-up, etc.).

The body 18b of the fluid-agitating element 18, which is at least partially magnetic or ferromagnetic, is sized to fit within the sidewall 34 defining the cavity 30 and, thus, is capable of rotating therein as the result of an externally-applied, non-contact motive force. The periphery of the sidewall 34 also defines a second receiver 26 for receiving a corresponding opening 24a in a motive device 24, which in view of the direct support provided by bearing 40 need only provide the force necessary to rotate the fluid-agitating element 18 in a non-contact fashion.

As should be appreciated, the embodiment shown in FIGS. 7a and 7b is the direct support counterpart for the embodiment shown in FIGS. 4a and 4b. The rigid portion 14 again includes a cavity 30 facing outwardly or toward the exterior of the bag 10 and a first receiver 16 for receiving and defining a home location for a fluid-agitating element 18. The first receiver 16 includes a bearing 40 for supporting the fluid-agitating element 18, which again is at least partially magnetic or ferromagnetic. The bearing 40 may be a slide bearing formed on the head end of a post 44 integral with the end wall 36 of the rigid portion 14 and adapted for fitting into an opening or recess 18a in the fluid-agitating element 18, or may be a different type of bearing for providing support therefor.

The motive device 24 includes a head end 24d adapted for insertion in a second receiver 26 defined by the cavity 30. This head end 24d preferably includes the drive structure DS that provides the force for causing the at least partially magnetic or ferromagnetic fluid-agitating element 18 to rotate about bearing 40. In FIGS. 7a and 7b, it is noted that the fluid-agitating element 18 includes an optional depending portion 18d that extends over the sidewall 34. As should be appreciated, this portion may also be magnetized or ferromagnetic such that a coupling is formed with the drive structure DS. A similar type of fluid-agitating element 18 could also be used in the levitation scheme of FIGS. 4a and 4b.

Various other modifications may be made based on the foregoing teachings. For example, FIGS. 8a and 8b show another possible embodiment of a vessel of the present invention for use in a fluid-agitating or mixing system. The vessel for holding the fluid is shown as being a bag 110 having a flexible portion 112, generally cylindrical in shape, and substantially or hermetically sealed from the ambient environment. In this embodiment, the bag 110 includes a first receiver 116 for receiving and holding the fluid-agitating element 118 at a home location. The first receiver 116 is in the form of a post 120 adapted to receive the fluid-agitating element 118, which has a corresponding opening 118a. The post 120 preferably includes an oversized head portion 120a that captures the fluid-agitating element 118, both before and after a fluid is introduced into the bag 110. Thus, the bag 110 may be manufactured, sealed (if desired), shipped, or stored prior to use with the fluid-agitating element 118 held in place on the post 120. The vessel 110 may also be sterilized as necessary for a particular application, and in the case of a flexible bag, may even be folded for compact storage. As should be appreciated, the post 120 also serves the advantageous function of keeping, holding, maintaining, or confining the fluid-agitating element 118 substantially at a home location or "centered," should it accidentally become decoupled from the adjacent motive device, which as described above may include a rotating superconducting element SE for not only providing the rotational force, but also a levitation force.

In this particular embodiment, the post 120 is shown as being defined by an elongated, rigid or semi-rigid, rod-like structure inserted through an opening typically found in the flexible plastic bags frequently used in the bioprocessing industry (pharmaceuticals, food products, cell cultures, etc.), such as a rigid or semi-rigid fitting or nipple 134. Despite the general rigidity of the post 120, the oversized portion 120a, which is shown as being T-shaped in cross-section, is preferably sufficiently thin and/or formed of a material that may flex or deform to easily pass through the opening in the nipple 134, as well as through the opening 118a in the fluid-agitating element 118. A conventional clamp 136, such as a cable tie, may be used to form a fluid-impervious seal between the nipple 134 and the post 120. Any other nipples or fittings present may be used for introducing the fluid F prior to mixing, retrieving a fluid during mixing or after mixing is complete, or circulating the fluid. Advantageously, the use of the rod/nipple combination allows for easy retrofitting. The oversized head portion 120a may be cross-shaped, L-shaped, Y-shaped, spherical, cubic, or may have any other shape, as long as the corresponding function of capturing the fluid-agitating element 118 is provided. The head portion 120a may be integrally formed, or may be provided as a separate component clamped or fastened to the post 120.

The bag 110 may also include a second receiver 126 that helps to ensure that proper alignment is achieved between the fluid-agitating element 118 and an adjacent structure, such as a support structure or a device for rotating and/or levitating the element. In the embodiment of FIGS. 8a and 8b, this second receiver 126 is shown as the opposite end 128 of the rod forming post 120. This end 128 of the rod may be inserted in a bore or opening 124a in an adjacent surface of a motive device 124 to assure proper alignment with the fluid-agitating element 118. In other words, as a result of the use of first and second receivers 116, 126, assurance is thus provided that the fluid-agitating element 118 is in the desired home or expected position for forming a coupling with an adjacent motive device 124.

FIG. 8a also shows the post 120 forming the first receiver 116 as projecting upwardly from a bottom wall of the vessel 110, but as should be appreciated, it could extend from any wall or other portion thereof. For example, as illustrated in FIG. 8b, the rod serving as both the first and second receivers 116, 126 may be positioned substantially perpendicular to a vertical plane. Specifically, in the particular embodiment shown, the bag 110 is positioned in a rigid or semi-rigid support container C having an opening O. Once the bag 110 is inserted in the container C, but preferably prior to introducing a fluid, the end 128 of the rod is positioned in the opening O such that it projects therefrom and may be inserted in the opening 124a formed in the motive device 124, which includes a superconducting element SE and may still levitate, and possibly rotate the at least partially magnetic fluid-agitating element 118 in this position. This ensures that the fluid-agitating element 118 is in the desired position to form the coupling necessary for levitation and/or rotation. Preferably, the portion of the rod extending outside the bag 110 and forming the second receiver 126 is greater in length than that in the embodiment shown in FIG. 1, and the depth of the opening 124a in the motive device 124 corresponds to this length. This in combination with the rigid or semi-rigid nature of the nipple 134 helps to ensure that the other end of the rod forming post 120 is properly aligned with the fluid-agitating element 118 when the magnetic coupling is formed.

Figure 9:
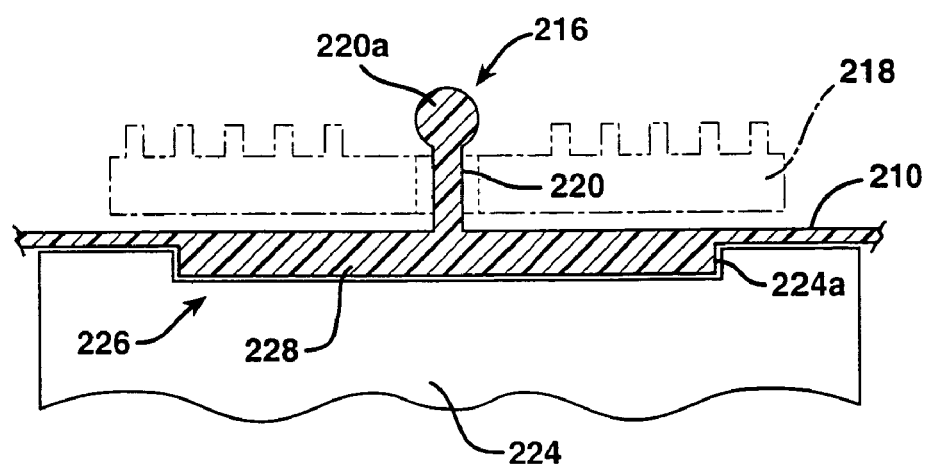
FIG. 9 is an enlarged, partially cross-sectional, partially cutaway side view of yet another embodiment of the vessel of the present invention.
Figure 9A:
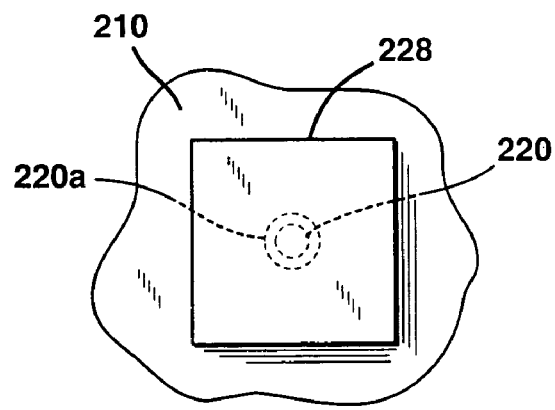
FIGS. 9a and 9b are cutaway bottom views of the vessel of FIG. 9a showing two different embodiments.
Figure 9B:
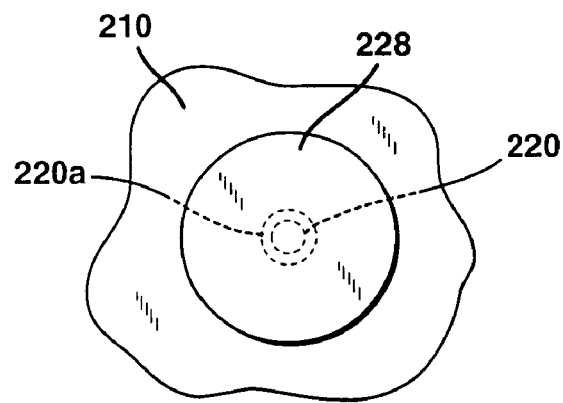

Other possible embodiments are shown in FIGS. 9-15. In FIG. 9, a first receiver 216 in the form of a post 220 includes an oversized spherical head 220a that serves to mechanically capture an adjacent fluid-agitating element 218 (shown in phantom). The post 220 is integrally formed with the vessel, which is preferably a bag 210 but may be partially or completely rigid. On the outer surface of the vessel 210, a low-profile second receiver 226 in the form of an outwardly-directed projection 228 is provided for receiving a corresponding portion 224a of the adjacent motive device 224. The projection 228 may have any shape desired, including square, circular, or the like (see FIGS. 9a and 9b), with the portion 224a having a corresponding shape. Once the projection 228 is aligns with and receives the corresponding portion 224a, the captive fluid-agitating element 218 is properly aligned with the adjacent motive device 224.

Another embodiment is shown in FIG. 10 in which the vessel 310 may be rigid or at least partially flexible. In this embodiment, the first receiver 316 is a post 320, which is shown merely for purposes of illustration as having an L-shaped head portion 320a for mechanically capturing an adjacent fluid-agitating element 318 (shown in phantom). The second receiver 326 is in the form of at least one projection 328 substantially concentric with the post 320. The projection 328 may be square, circular, or may have any other desired shape. The projection may also be continuous, as shown in FIG. 10a, or interrupted to form segments 328a, 328b...328n, as shown in FIG. 10b. Although a plurality of segments are shown, it should be appreciated that the number of segments provided may be as few as one, regardless of the shape of the projection 328 (and could even be a single stub offset from the post 320). The corresponding portion 324a of the motive device 324 that is received by the second receiver 326 is similarly shaped and preferably continuous, but could also have one or more segments matching the segments in the vessel 310 (including a single offset bore).

Figure 11:
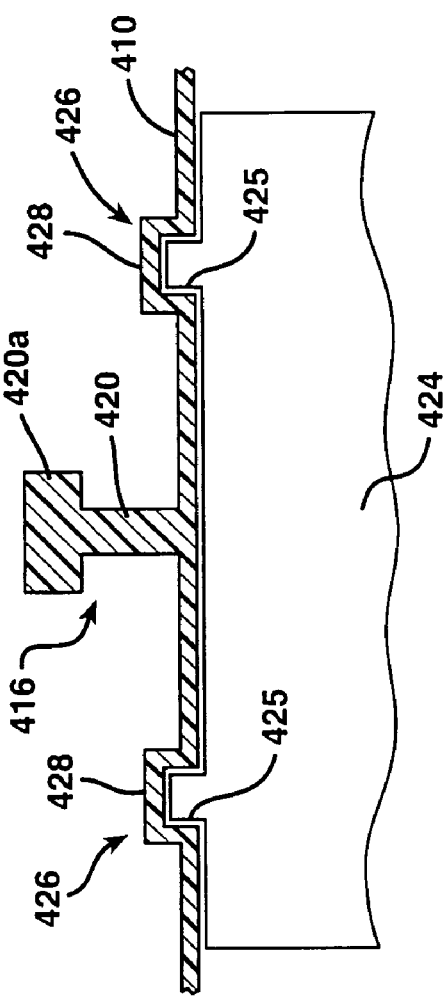
FIG. 11 is an enlarged, partially cross-sectional, partially cutaway side view of another embodiment of the vessel of the present invention.
Figure 11A:
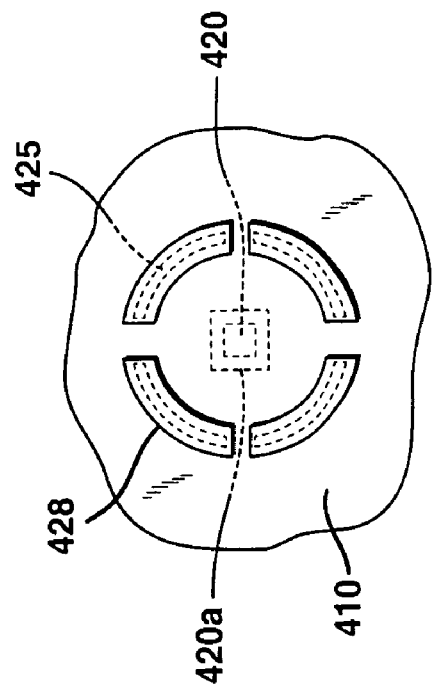
FIGS. 11a and 11b are cutaway bottom views of the vessel of FIG. 11 showing two different embodiments.
Figure 11B:
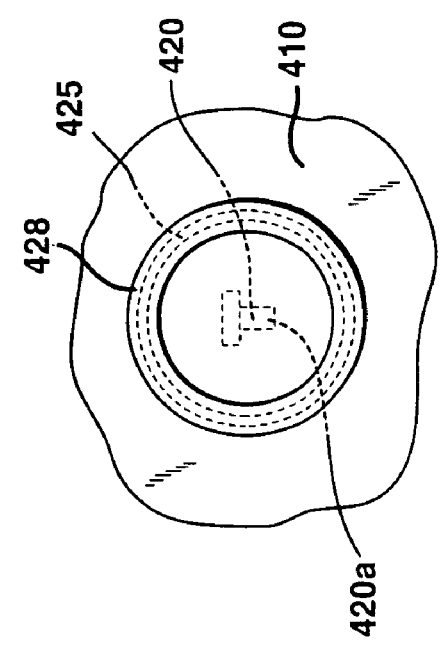

In the embodiment of FIG. 11, the vessel 410 includes a first receiver 416 in the form of a post 420, again shown with an oversized T-shaped head 420a. The second receiver 426 includes at least one channel, recess, or groove 428 formed in the vessel 410. A corresponding projection 425 is provided in the motive device 424 for engaging the channel, recess or groove 428 to provide the desired alignment function, such as between driving magnets and driven magnets, between driven magnets and a rotating superconducting element, or between any other driver and a driven structure associated with a fluid-agitating element. The channel, groove, or recess 428 is preferably continuous (see FIG. 11a, with the projection 425 shown in phantom), but may be segmented as well (see FIG. 11b).

Figure 12:
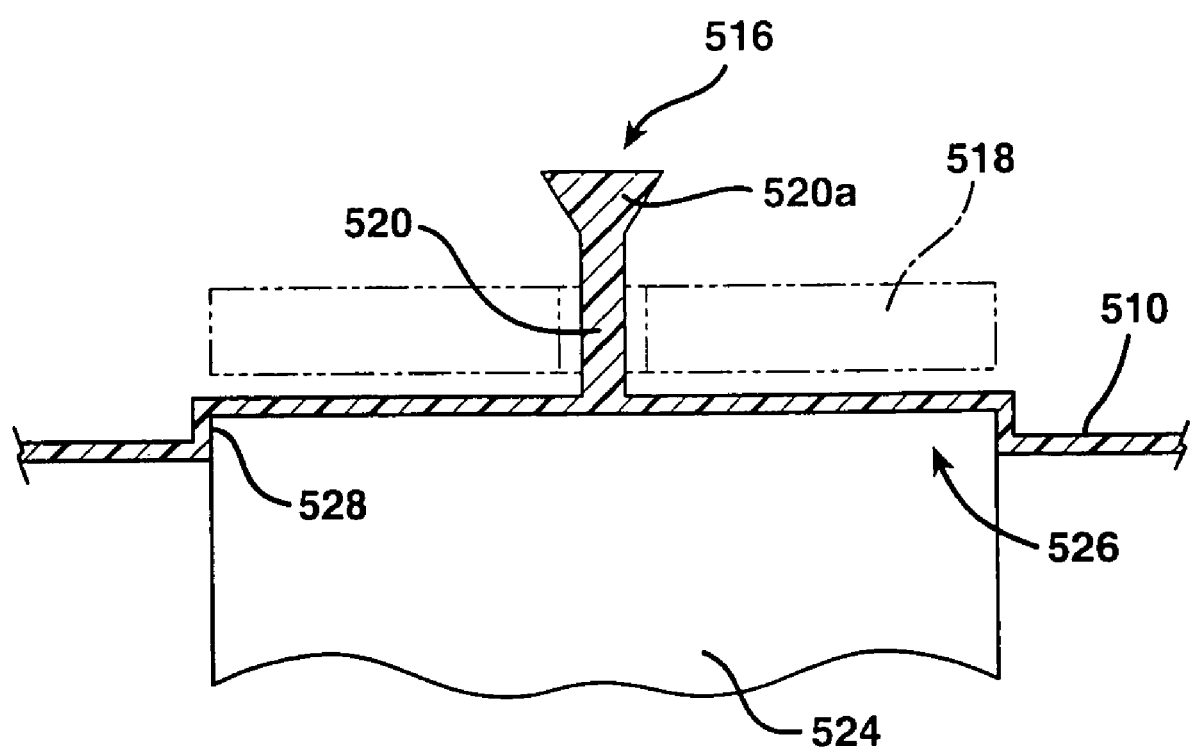
FIG. 12 is an enlarged, partially cross-sectional, partially cutaway side view of still another embodiment of the vessel of the present invention.

Yet another embodiment is shown in FIG. 12. In this embodiment, the vessel 510 again includes a first receiver 516 in the form of a post 520, which is shown for purposes of illustration as having a frusto-conical head to create a Y-shaped cross-section. The second receiver 526 is in the form of a low-profile recessed portion 528 formed in the vessel 510. This recessed portion 528 is sized and shaped for receiving a portion of the motive device 510, and thus ensures that the proper alignment is achieved between a fluid-agitating element 518 concentric with the post 520 and any structure for levitating and/or rotating the element. As with the embodiments described above, the recessed portion 528 may have any shape desired, including square, circular, triangular, rectangular, polygonal, or the like.

Figure 13:
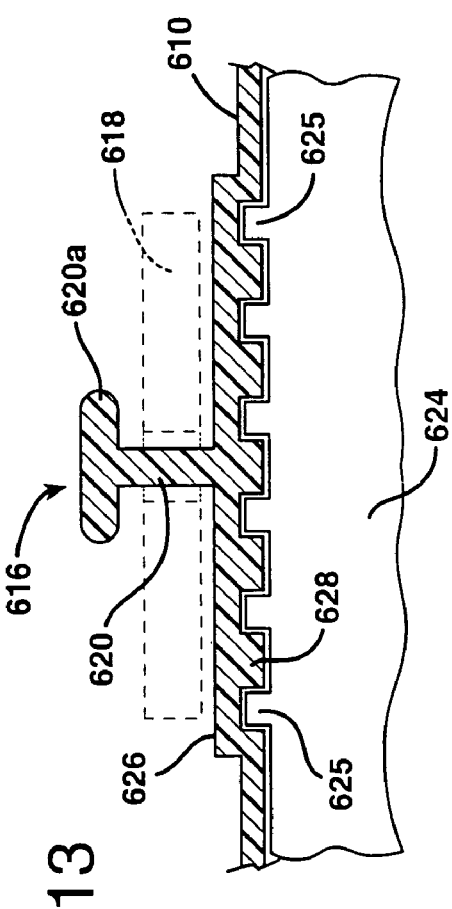
FIG. 13 is an enlarged, partially cross-sectional, partially cutaway side view of still another embodiment of the vessel of the present invention.
Figure 13B:
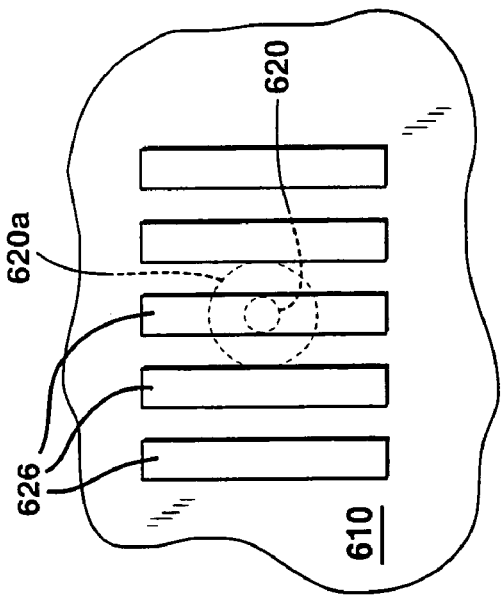
FIGS. 13a and 13b are cutaway bottom views of the vessel of FIG. 13 showing two different embodiments.
Figure 13A:
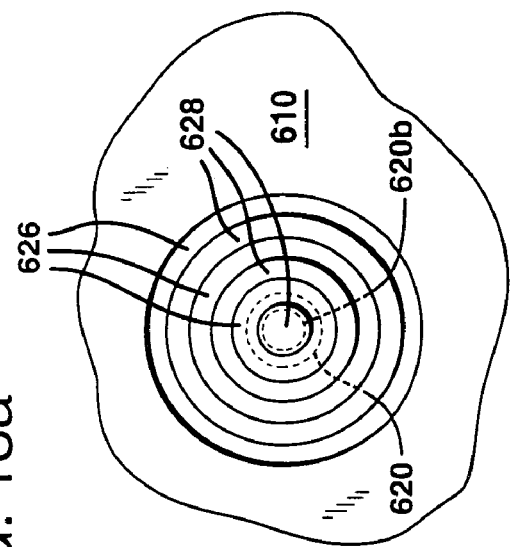

FIG. 13 illustrates an embodiment wherein the vessel 610 is provided with a first receiver 616 in the form of a post 620 having a head 620a (shown as disc-shaped), as well as a plurality of structures 628 defining second receivers 626 adapted for receiving a portion of an external structure, such as a projection 625 formed on an end face of a motive device 624. The second receivers 626 may be in the form of concentric ring-shaped recesses 628, as illustrated in FIG. 13a, but could also comprise concentric squares or even arrays of straight lines, as shown in FIG. 13b. Three second receivers 626 are shown in FIGS. 13 and 13a, but it should be appreciated that more or fewer may be provided as desired. Indeed, the number of structures provided may be used as an indicator of the size, shape, or other characteristic of the fluid-agitating element 618 in the vessel 610, which thus allows the user to select a suitable motive device (such as one having a superconducting element having a particular characteristic).

Figure 14:
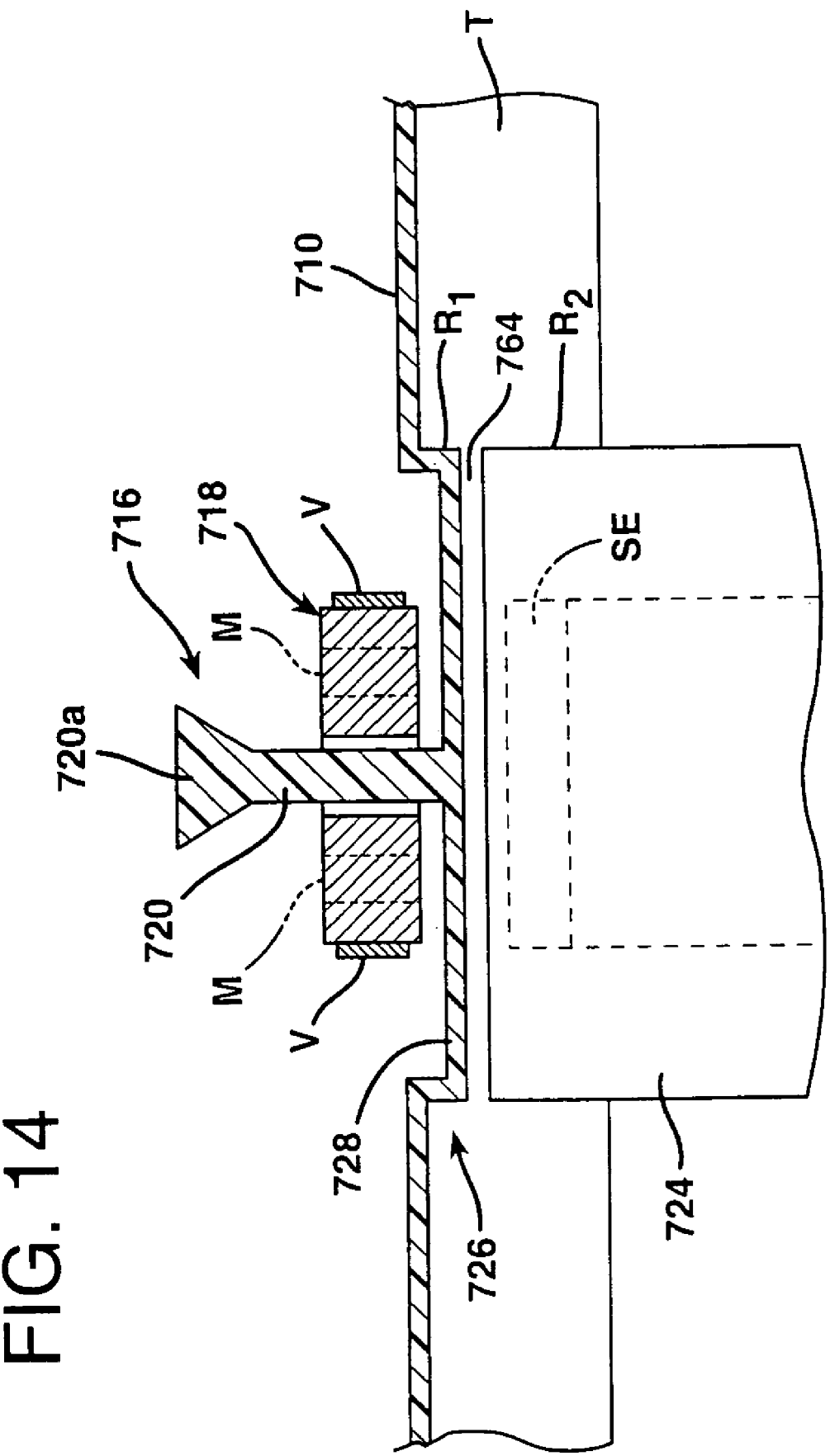
FIG. 14 is an enlarged, partially cross-sectional, partially cutaway side view of yet another embodiment of the vessel of the present invention.

FIG. 14 shows an embodiment wherein the vessel 710, which again may be rigid or partially flexible, includes a first receiver 716 in the form of a post 720 having an oversized head portion 720a and a second receiver 726 in the form of a hat or cup-shaped projection 728 (which may be integrally formed or a separate rigid portion). The second receiver 726 receives a portion of an intermediate support structure T including a first recess $R_1$ on one side and a second recess $R_2$ on the opposite side. The second recess $R_2$ is adapted for receiving at least a portion of the motive device 724, which is shown as a cryostat including a rotating, thermally isolated superconducting element SE for coupling with at least two alternating polarity magnets M (or alternatively, the head of the cryostat may be attached to a bearing positioned in recess $R_2$ and rotated). This particular embodiment dispenses with the need for forming a locator bore in the motive device 724 to align the fluid-agitating element 718 therewith (although it remains possible to provide such a bore for receiving a projection on the support structure T to achieve the alignment function). Generally, it is of course desirable to form the wall 764 between the recesses $R_1$, $R_2$ as thin as possible to enhance the stiffness of the coupling used to rotate and/or levitate the fluid-agitating element 718 (which includes vanes V).

Figure 15:
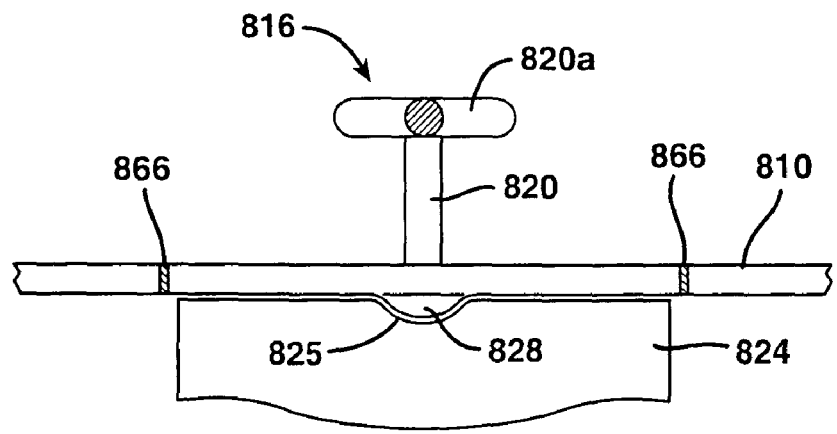
FIG. 15 is an enlarged, partially cross-sectional, partially cutaway side view of a further embodiment of the vessel of the present invention.
Figure 15A:
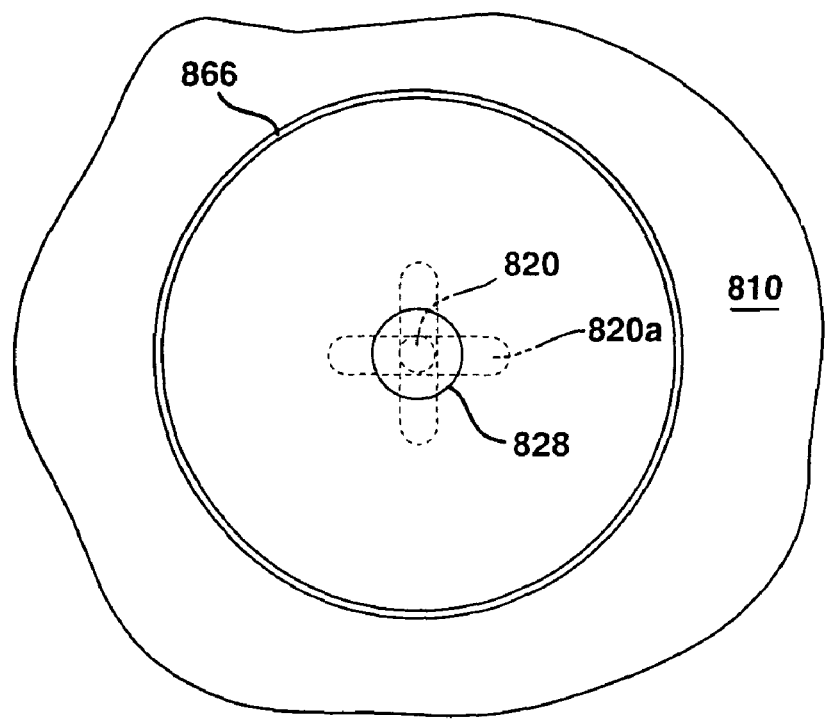
FIG. 15a is a bottom view of the vessel of FIG. 15 showing two different embodiments.

FIG. 15 shows an embodiment where a second receiver 826 in the form of a slightly raised projection 828 is provided in the vessel 810 that corresponds to a dimple 825 formed in an external structure, such as the end face of the motive device 824. As should be appreciated, the opposite arrangement could also be used, with the dimple formed in the vessel 810 and serving as a second receiver 826. Optionally, or instead of the projection 828/dimple 825 combination, at least one indicia may be provided to allow an observer to determine the proper location of the structure such as motive device 824 relative to the vessel 810. The indicia is shown as a darkened ring 866 formed in the outer wall of the vessel 810, which could be a bag or a rigid or semi-rigid container. However, it should be appreciated that the indicia could be in the form of one or more marks placed on or formed in the outer surface of the vessel 810 (including even possibly a weld or seal line), or even marks placed on the opposite sides of an intermediate support surface (not shown). In any case, the indicia 866 is preferably designed such that it helps to align the motive device 824 relative to a first receiver 816 in the vessel 810 for receiving and defining a home location for a fluid agitating element, such as the post 820 (which is shown having a cross-shaped head 820a). The indicia 866 thus helps to ensure that the fluid-agitating element is aligned with any driving or levitating structure held therein.

Figure 17:
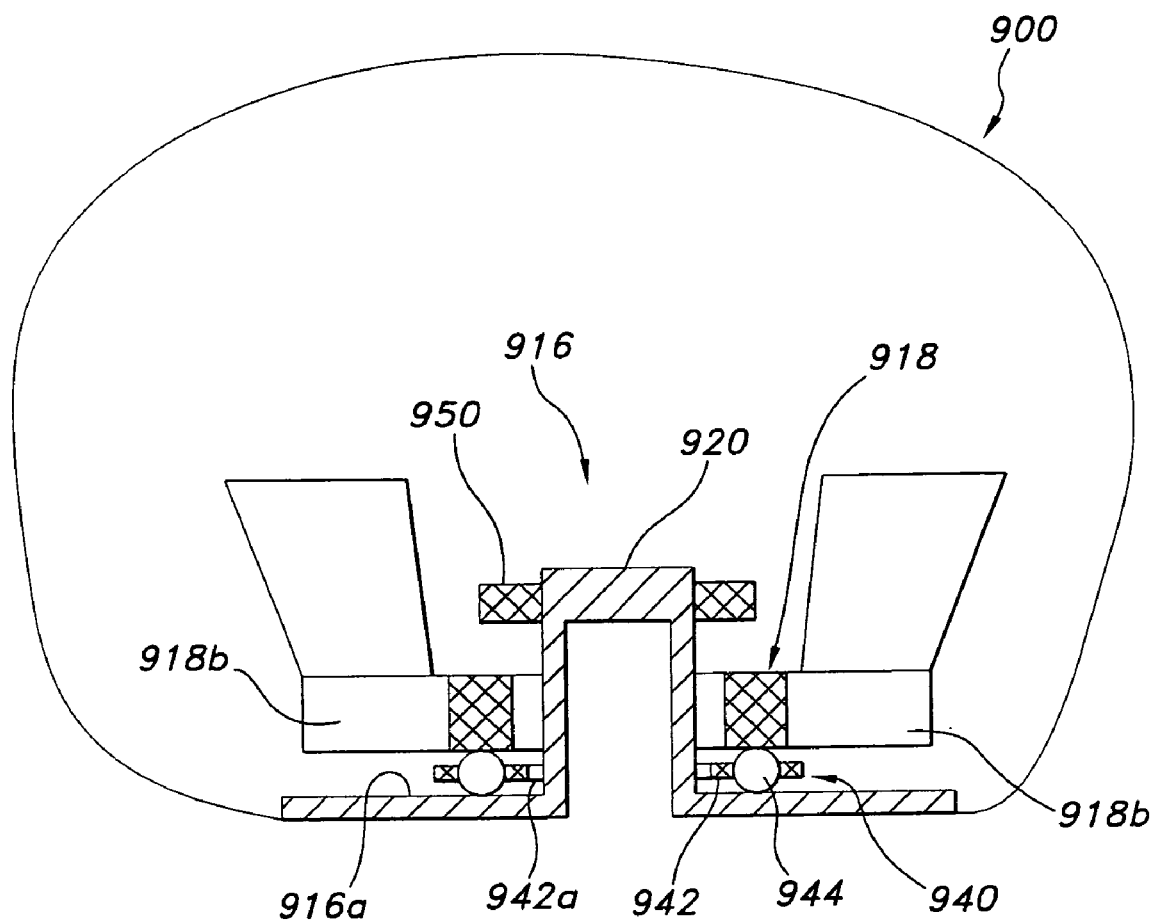
FIG. 17 illustrates one embodiment of an arrangement including a roller bearing for supporting the fluid-agitating element.

FIG. 17 illustrates an embodiment in which the vessel is in the form of a collapsible bag 900 including a rigid portion defining a first rigid receiver 916 with a post 920 projecting toward an interior compartment of the bag. Adjacent the post 920, and thus associated with the receiver 916 forming a portion of the bag (a collapsible vessel), is a low-friction bearing 940 for supporting the fluid-agitating element 918. Preferably, this bearing 940 is a separate structure from the post 920 (and thus may bodily rotate relative to it or, in other words, rotate as a whole), and includes a retainer (such as a ring 942) and a plurality of discrete roller elements. The fluid-agitating element 918 may be of the type described above and shown in FIG. 1, and thus includes a magnet 918b for connecting with an external drive structure (not shown) via magnetic coupling in order to induce rotation at the desired speed.

The post 920 in the illustrated embodiment projects through an opening 942a in the ring 942 forming part of the bearing 940. This ring 942, in turn, supports the plurality of roller elements, such as spherical roller balls 944 (and thus forms a ball thrust bearing, although a roller thrust bearing could also be used in this embodiment). These balls 944 at least engage a corresponding rigid seating surface 916a associated with the receiver 916, and preferably project from both sides of the ring 942 in an opposed fashion so as to also engage a corresponding surface of the fluid-agitating element 918 and provide the desired low-friction support therefor. A separate locking element 950 associated with the post 920 (including possibly by way of friction fit, snap fit, or threaded engagement) may retain or capture the fluid-agitating element 918 and bearing 940 in place.

In use, a magnetic coupling may be formed between a selected external motive device (such as a "mag" drive or otherwise) to rotate the fluid agitating element 918. As the rotation is effected, the fluid agitating element 918 thus engages the bearing 940, which provides desirable low-friction support. This is the case even if the balls 944 only project toward and engage the rigid seating surface 916*a* of the receiver 916.

Preferably, the bearing 940 is made of low cost, lightweight, disposable materials. Thus, when the pumping or mixing operation is complete, the bearing 940 can simply be discarded, along with the vessel (e.g., a polymer bag). Alternatively, the bearing 940 may be made of materials that can be easily sterilized and re-used in a different pumping or mixing operation, such as stainless steel.

The engagement surfaces of the receiver 916 and fluid-agitating element 918 may be made of plastic, which depending on the conditions may be subject to wear and the creation of deleterious wear particles. To avoid this, it is possible to interject a wear-resistant (e.g., metal or stainless steel) surface or plate (not shown) between either the adjacent surface of the fluid-agitating element 918, the seating surface 916*a*, or both. This arrangement provides suitable contact surface(s) for the rolling elements of the bearing 940.

Figure 18:
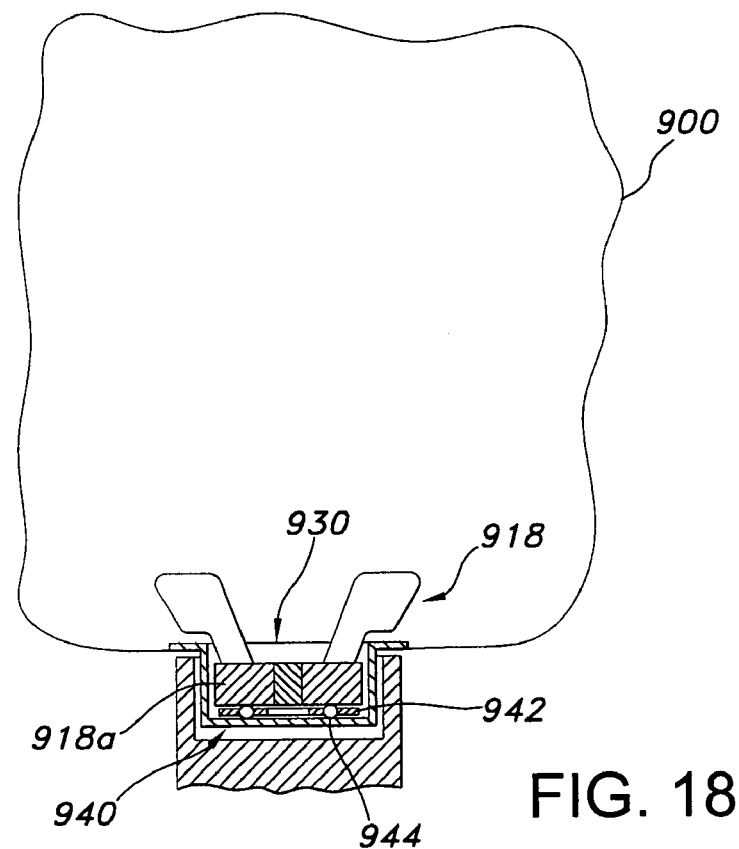
FIGS. 18-23 illustrate other embodiments of support arrangements with a roller bearing for supporting the fluid-agitating element.

An alternative embodiment of the roller bearing 940 is shown in FIG. 18. In this embodiment, the rigid receiver 916 is cup-shaped and includes a cavity 930 in communication with the interior compartment of the vessel 900 for receiving the fluid-agitating element 918. The low-friction roller bearing 940 in the form of a ball thrust bearing is inserted in the cavity 930 but remains a separate structure, as with the embodiment of FIG. 17, and thus bodily rotates relative to the receiver 916.

Figure 19:
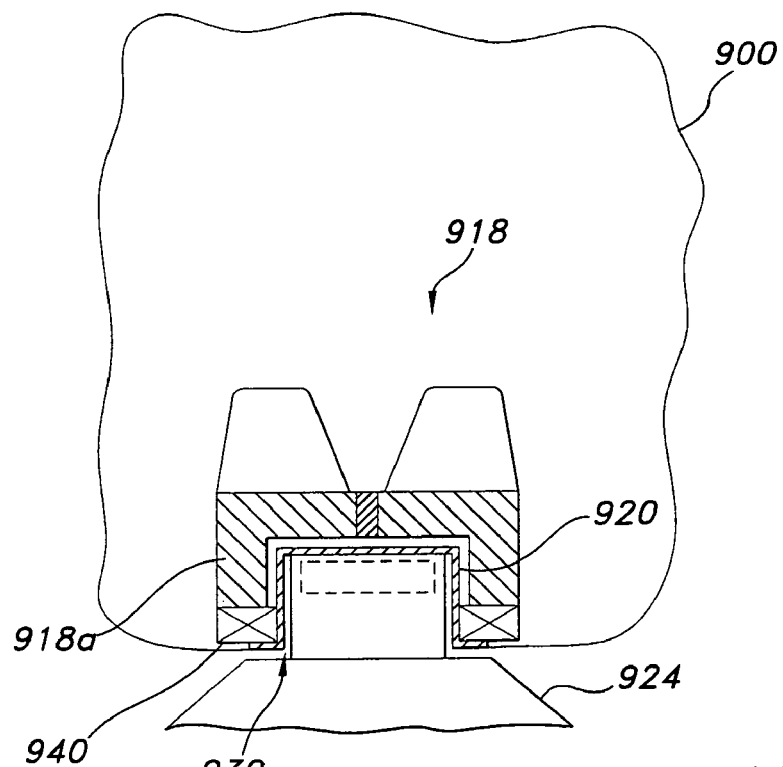
Figure 20:
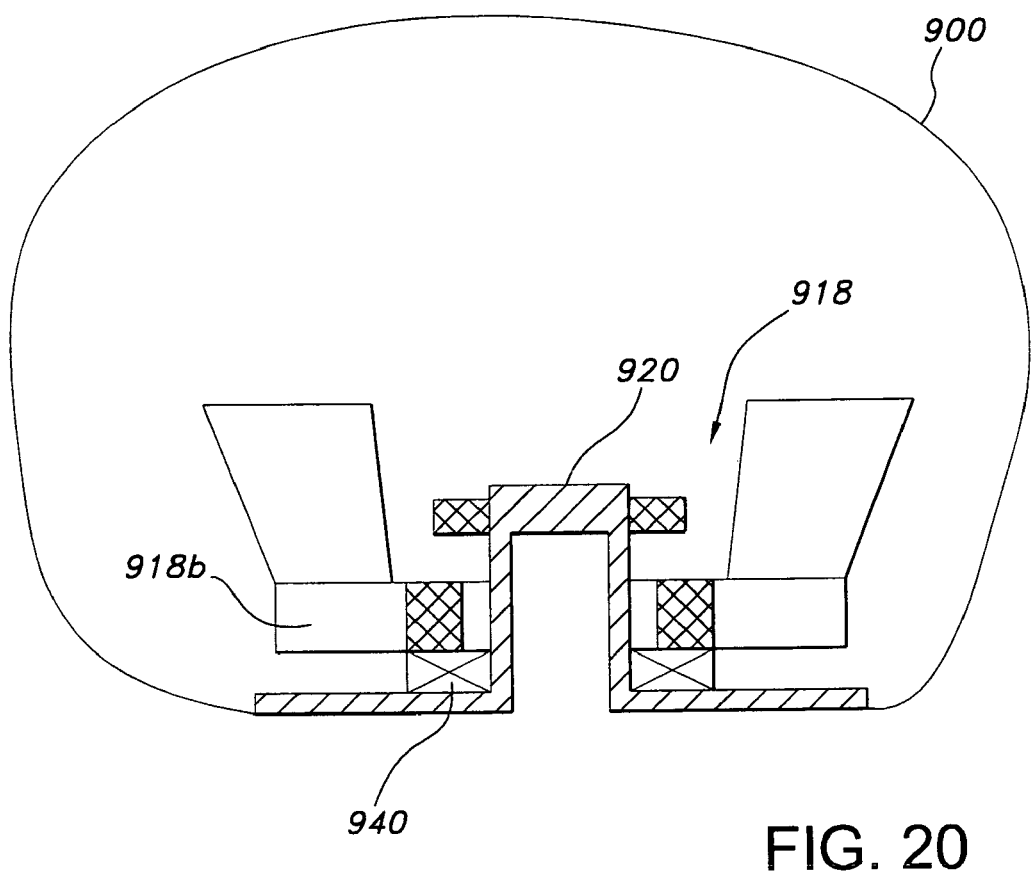
Figure 21:
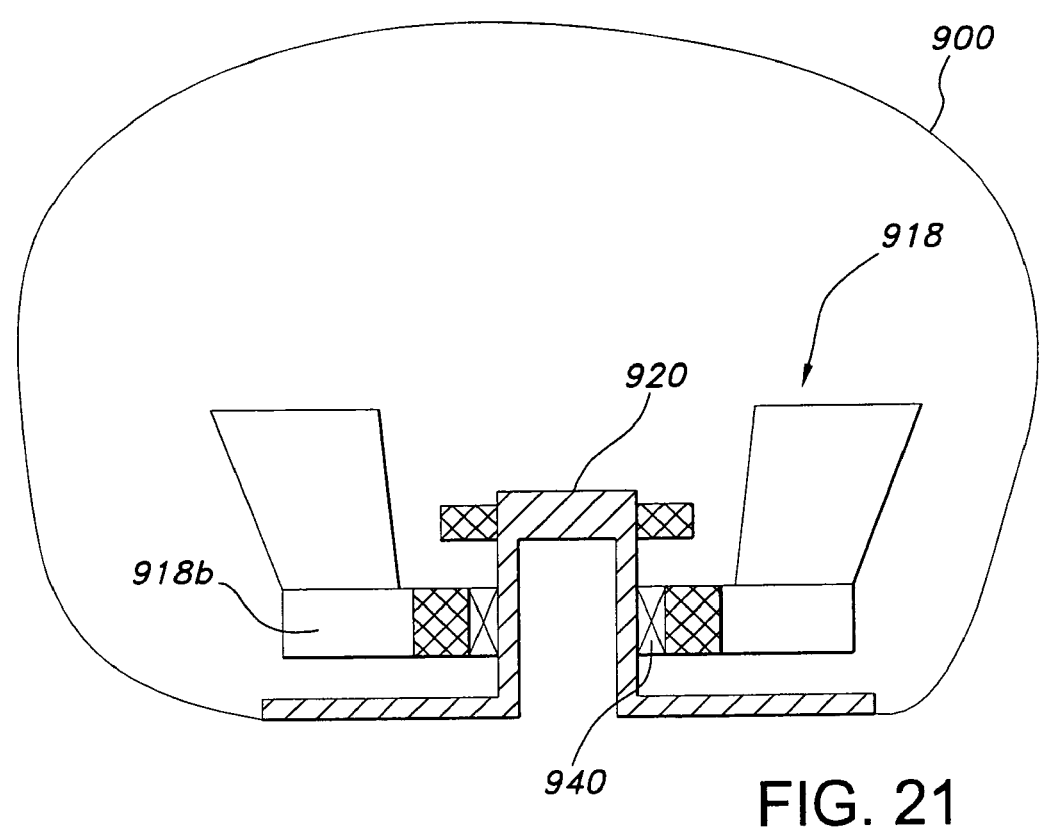

In FIG. 19, a roller bearing 940 is also provided, but with an embodiment in which the rigid receiver 916 is cap-shaped and projects inwardly toward the interior compartment of the vessel 900. Unlike the embodiments of FIGS. 17 and 18, the roller bearing 940 is in the form of a ball bearing, which may include one race (such as the inner race, not shown) attached or mounted to the sidewall of a receiver 916 with the cavity 930 (which is shown as being sized for receiving an external motive device 924) and the other race (such as the outer race, not shown) attached or mounted to the fluid-agitating element 918. FIGS. 20 and 21 illustrate alternative embodiments in which a roller bearing 940, again preferably in the form of a ball bearing, is attached directly to the receiver 916 (such as along the seating surface) and the post 920, respectively.

Figure 22:
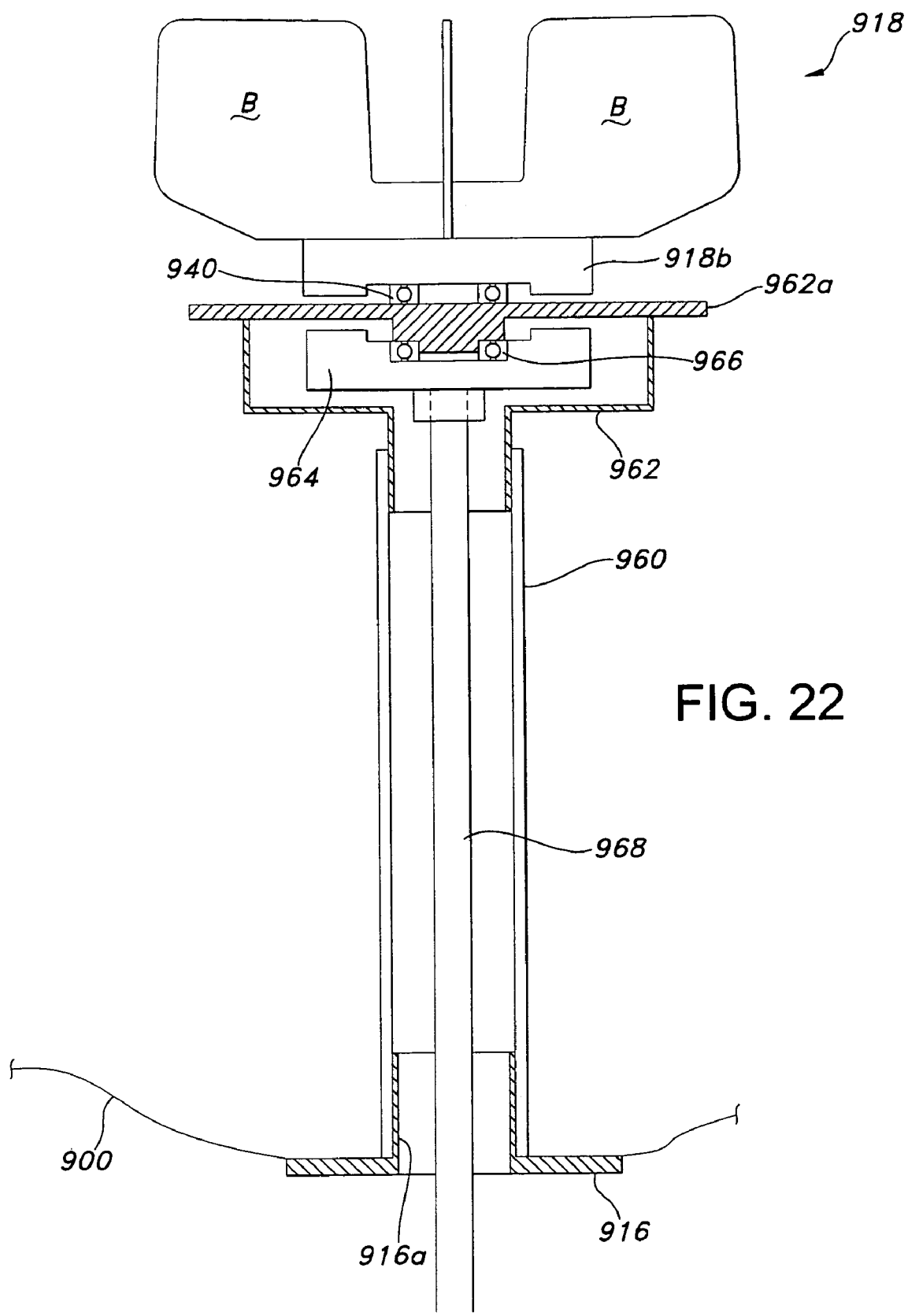
Figure 23:
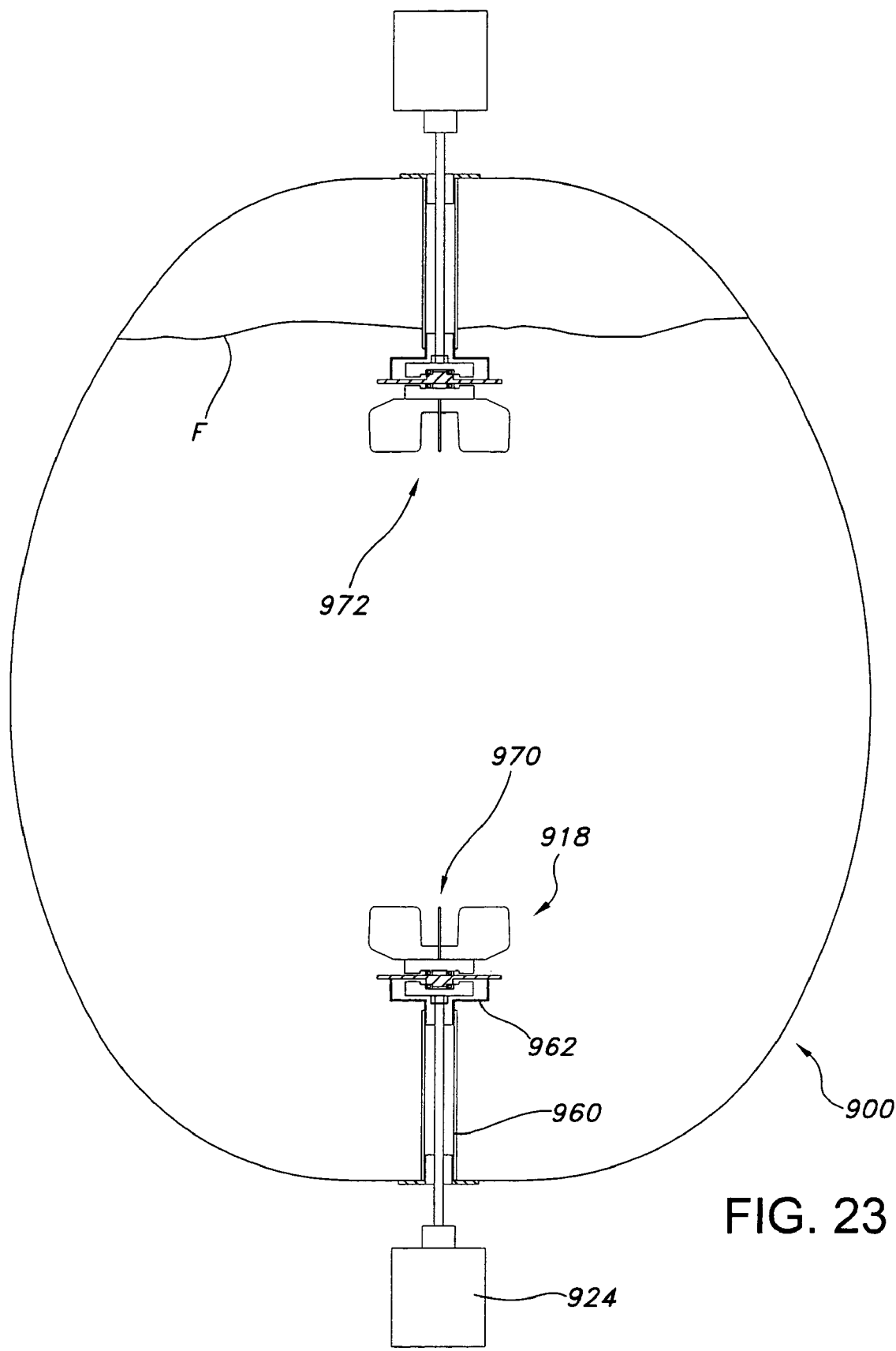

FIGS. 22 and 23 illustrate another embodiment of a fluid-agitating element 918 associated with a roller bearing 940 in a vessel, such as a collapsible bag 900. The bag includes a flexible portion defining an interior compartment or chamber and a rigid receiver 916 including a post 916*a* defining an open passage. A fluid-agitating element 918 also in the interior compartment includes an at least partially magnetic or ferromagnetic body 918*b*, and preferably further includes blades B or vanes.

The post 916*a* connects to a tube or sleeve 960 projecting into the interior compartment of the bag (and thus into any fluid present in the adjacent space). The sleeve 960, which is preferably flexible, in turn attaches to a rigid drive housing 962 for housing a drive magnet 964 for forming a magnetic coupling with the fluid-agitating element 918. Preferably, the fluid-agitating element 918 is supported by the roller bearing 940, which is in turn mounted directly to and received by a sidewall 962*a* of the drive housing 962. The drive magnet 964 in the housing 962 is preferably also supported by a bearing and, most preferably, a roller bearing 966 attached or mounted to the housing 962. Alternatively, the arrangement of FIG. 17 could be used, including a roller bearing that bodily rotates about a post for receiving the fluid-agitating element.

In use, a rigid drive rod or shaft 968 is passed through the opening 916*a* and the sleeve 960 to engage the drive magnet 964. The engagement may be by way of a mechanical coupling with the corresponding end of the shaft 968, such as for example, threaded engagement (note phantom lines), a bayonet fitting, or like mechanical coupling means that is capable of transmitting rotational motion. The opposite end of the shaft 968 extends outside of the vessel 900 or bag, and may be coupled to a motive device 924, such as a variable speed electric drive motor (see FIG. 23).

As a result of this arrangement, the fluid-agitating element 918 may be rotated in the collapsible vessel 900 without the need for any opening or drive shaft passing therethrough. This of course allows for a sterile environment to be maintained, if desired (such as when the vessel 900 is used in a sealed bioreactor environment for culturing cells or like bioprocessing techniques). In such case, the seals between the flexible portion of the bag 900, the receiver 916, the tube 960, and the housing 962 should all be hermetic and may be formed using well-known types of plastic joining techniques.

As should be appreciated, once the mixing operation is complete, the shaft 968 may be detached from the magnet 964 and then subsequently used in a different mixing operation (such as with a different vessel; not shown). In such instance, the vessel 900 may simply be discarded, including the drive magnet 964, associated housing 962, tube 960, receiver 916, fluid-agitating element 918, and roller bearings 940, 966. Alternatively, the vessel 900 or any of the associated structures may be re-used, typically after a thorough cleaning and/or re-sterilization.

FIG. 23 illustrates an embodiment in which two of the mixers of FIG. 22 are associated with a single vessel 900 or bag (which would typically be supported by a rigid frame, stand, container or the like, which may thus include one or more openings in one or more sidewalls through which the shafts 968 pass). In the illustrated embodiment, a first mixer 970 including the elements shown in FIG. 22 projects upwardly from a floor or bottom portion of the vessel 900, while the second mixer 972 projects from the top portion. The mixers 970, 972 thus have independently rotatable fluid-agitating elements 918. Most preferably, the two mixers 970, 972 are opposed. Thus, when the vessel 900 is substantially filled with fluid (note line F in FIG. 23) such that the corresponding fluid-agitating elements of the mixers 970, 972 are submerged, gentle yet thorough mixing may be provided. This type of thorough mixing is especially advantageous when the vessel 900 is used as a bioreactor in which cells are cultured.

Obvious modifications or variations are possible in light of the above teachings. For example, instead of forming the rigid portion 14 as part of the bag 10 by forming a seal at an interface between the two, it could also be positioned in contact to an inner or outer surface of the bag and attached using vacuum-forming techniques, adhesives, or the like. For example, in the cap-shaped embodiment of FIG. 3*a*, the bag 10 would essentially line the inside surfaces of the sidewall 34 and end wall 36 (see FIG. 16*a*). Likewise, in the embodiment of FIG. 4*a*, the bag 10 would cover the sidewall 34 and end wall 36 (see FIG. 16*b*). In both cases, the need for the flange 22 may be eliminated. It is also possible to provide any of the first receivers with a tapered or frusto-conical engagement surface that mates with a corresponding surface on the fluid-agitating element, as disclosed in my co-pending patent application Ser. No. PCT/US01/31459, the disclosure of which is incorporated herein by reference. Also, instead of the two mixers 970, 972 being identical, two different types of mixers could be used (such as, for example, the embodiment of FIG. 22 in combination with the embodiment including a magnetic fluid-agitating element levitated by a superconducting element, as shown in FIG. 2 and described in detail in U.S. Pat. No. 6,758,593, the disclosure of which is incorporated herein by reference). The arrangement could also be the embodiment of either FIG. 2 or 22 and the wand mixer shown in U.S. Pat. No. 6,494,613, which is also incorporated herein by reference).

The foregoing descriptions of various embodiments of the present inventions have been presented for purposes of illustration and description. These descriptions are not intended to be exhaustive or to limit the invention to the precise forms disclosed. The embodiments described provide the best illustration of the principles of the invention and its practical applications to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. An apparatus intended for receiving a fluid and a rotatable fluid-agitating element, comprising:
    a collapsible bag including an interior compartment capable of receiving and holding the fluid and the fluid-agitating element; and
    a roller bearing adapted for providing low-friction support for the fluid-agitating element in the interior compartment of the bag.

2. The apparatus according to claim 1, wherein the bag includes a cap-shaped receiver for receiving the fluid-agitating element that projects toward an interior compartment of the bag, thereby forming an external cavity.

3. The apparatus according to claim 1, wherein vessel includes a cup-shaped receiver that forms a cavity in communication with the interior compartment of the bag for at least partially receiving the roller bearing and the fluid-agitating element.

4. The apparatus according to claim 1, wherein the bag includes a rigid receiver that supports the fluid-agitating element.

5. A method of forming an assembly for agitating a fluid, comprising:
    providing a collapsible bag for receiving a magnetic fluid-agitating element; and
    supporting the fluid-agitating element on a roller bearing in the bag.

6. The method of claim 5, wherein the bag includes a post, the roller bearing includes an opening, and the supporting step comprises placing the post through the opening.

7. The method of claim 5, further comprising attaching the roller bearing to a rigid receiver attached to the bag.

8. The method of claim 7, wherein the rigid receiver is cap-shaped and includes a sidewall for supporting the roller bearing.

9. The method of claim 7, wherein the rigid receiver is cup-shaped and includes a cavity in communication with an interior compartment of the bag, and the method includes the step of positioning the roller bearing in the cavity.

10. An apparatus intended for receiving and agitating a fluid, comprising:
    a collapsible bag including an interior compartment for receiving the fluid; and
    a magnetic fluid-agitating element positioned in the interior compartment of the bag;
    wherein the bag includes a tube extending into the interior compartment and supports a roller bearing for use in rotating the fluid-agitating element in the bag.

11. The apparatus according to claim 10, wherein the bearing is exterior to the interior compartment of the bag.

12. A method of positioning a fluid-agitating element in a bag intended for receiving a fluid in need of agitation, comprising:
    supporting the fluid-agitating element in the vessel with a roller bearing that bodily rotates relative to the bag.

13. The method of claim 12, wherein the bag includes a post, the bearing is a ball thrust bearing including an opening, and the method comprises placing the post through the opening before the supporting step.

14. The method of claim 12, wherein the bag includes a cavity, and the method comprises placing the bearing in the cavity.

15. The method of claim 12, wherein the bearing includes a plurality of roller elements, and the supporting step comprises simultaneously contacting both the fluid-agitating element and the bag with the plurality of roller elements.

16. An apparatus intended for receiving and mixing a fluid, comprising:
    a fluid-agitating element;
    a collapsible bag capable of receiving the fluid and the fluid-agitating element; and
    a roller bearing for providing low-friction support for the fluid-agitating element.

17. An apparatus intended for receiving and mixing a fluid, comprising:
    a magnetic fluid-agitating element;
    a bag capable of receiving the fluid, said bag including a flexible wall carrying a rigid receiver for receiving the fluid-agitating element; and
    a bearing for providing low-friction support for the magnetic fluid-agitating element.

18. The apparatus of claim 17, wherein the bearing comprises a first race connected to the fluid-agitating element, a second race connected to the rigid receiver, and a plurality of rolling elements adapted for engaging the first and second races.

19. The apparatus of claim 17, wherein the bearing comprises a thrust bearing.

20. The apparatus of claim 17, wherein the rigid receiver includes a peripheral flange forming a support surface for the second race.

21. The apparatus of claim 20, wherein the peripheral flange of the rigid receiver is attached to the flexible wall of the bag.

22. The apparatus of claim 20, wherein the rigid receiver comprises a projection extending inwardly into an interior compartment of the vessel.

23. An apparatus intended for receiving and agitating a fluid, comprising:
    a flexible bag having an interior compartment adapted for receiving the fluid under sterile conditions; and
    a rotatable fluid-agitating element positioned in the interior compartment;
    wherein the bag includes a wall forming a cavity and a bearing adapted for promoting rotation of the fluid-agitating element.

24. The apparatus of claim 23, wherein the bearing comprises a roller bearing connected to the wall of the bag.

25. The apparatus of claim 23, wherein the cavity is at least partially bounded by a rigid wall that supports the fluid agitating element in the bag.

26. The apparatus of claim 23, further including a motive device for positioning in the cavity to cause rotation of the fluid-agitating element.

27. The apparatus of claim 23, wherein the bearing is positioned in the cavity.

28. An apparatus intended for receiving and mixing a fluid, comprising:
 a fluid-agitating element;
 a bag having an interior compartment capable of receiving the fluid and the fluid-agitating element under sterile conditions;
 a shaft projecting into the interior compartment for driving the fluid-agitating element; and
 at least one roller bearing associated with the shaft.

29. The apparatus of claim 28, further including a non-contact coupling for rotating the fluid-agitating element.

30. The apparatus of claim 29, wherein the shaft depends from an upper portion of the bag.

31. The apparatus of claim 30, wherein the non-contact coupling comprises a magnetic coupling.

32. The apparatus of claim 28, wherein the roller bearing comprises a ball bearing.

33. The apparatus of claim 28, further including a rigid receiver for supporting the shaft.

34. The apparatus of claim 28, wherein the shaft comprises a tubular structure.

* * * * *